United States Patent
Barlow et al.

(10) Patent No.: US 9,037,266 B2
(45) Date of Patent: May 19, 2015

(54) ENHANCED THERAPEUTIC STIMULUS FOR NON-NUTRITIVE SUCK ENTRAINMENT SYSTEM AND METHOD

(75) Inventors: Steven M. Barlow, Lawrence, KS (US); David L. Stalling, Shawnee, KS (US); Kenneth Aron, Shawnee, KS (US)

(73) Assignee: Innara Health, Inc., Olathe, KS (US)

( * ) Notice: Subject to any disclaimer, the term of this patent is extended or adjusted under 35 U.S.C. 154(b) by 505 days.

(21) Appl. No.: 13/457,203

(22) Filed: Apr. 26, 2012

(65) Prior Publication Data

US 2012/0209148 A1 Aug. 16, 2012

Related U.S. Application Data

(63) Continuation-in-part of application No. 12/390,142, filed on Feb. 20, 2009, now Pat. No. 8,226,579.

(60) Provisional application No. 61/036,304, filed on Mar. 13, 2008, provisional application No. 61/030,484, filed on Feb. 21, 2008.

(51) Int. Cl.
*A61N 1/00* (2006.01)
*A61B 5/03* (2006.01)
(Continued)

(52) U.S. Cl.
CPC ............... *A61B 5/038* (2013.01); *A61B 5/486* (2013.01); *A61B 5/682* (2013.01); *A61B 5/6896* (2013.01); *A61H 23/02* (2013.01); *A61H 2201/5005* (2013.01); *A61H 2201/5007* (2013.01); *A61H 2201/5071* (2013.01); *A61H 2205/022* (2013.01)

(58) Field of Classification Search
CPC . A61N 1/0548; A61N 1/3601; A61N 1/3611; A61N 1/3605
USPC .................................. 607/134, 142; 600/590
See application file for complete search history.

(56) References Cited

U.S. PATENT DOCUMENTS

| 4,232,687 A | 11/1980 | Anderson-Shanklin |
| 5,830,235 A | 11/1998 | Standley |
| 6,033,367 A | 3/2000 | Goldfield |

(Continued)

FOREIGN PATENT DOCUMENTS

| CN | 101080195 B1 | 11/2012 |
| EP | 1786319 B1 | 10/2012 |

(Continued)

OTHER PUBLICATIONS

Barlow et al, "Synthetic orocutaneous stimulation entrains preterm infants with feeding difficulties to suck." J Perinatol, 2008, pp. 541-548, vol. 28, No. 8.

(Continued)

*Primary Examiner* — Christopher D Koharski
*Assistant Examiner* — Philip Edwards
(74) *Attorney, Agent, or Firm* — Polsinelli PC

(57) ABSTRACT

The present invention relates to a system and method for using the system. In particular, the present invention relates to an application, executable by a processing device to assess the organization of a non-nutritive suck (NNS) pattern of a patient and to entrain an organized NNS pattern in the patient. The software system receives data from an orofacial stimulation appliance to assess the patient's natural NNS pattern and generates a precise therapeutic pulse profile that is actuated as a tactile stimulus via the orofacial stimulation appliance to entrain an organized NNS pattern.

46 Claims, 22 Drawing Sheets

(51) Int. Cl.
*A61B 5/00* (2006.01)
*A61H 23/02* (2006.01)

(56) References Cited

U.S. PATENT DOCUMENTS

| | | |
|---|---|---|
| 7,435,232 B2 | 10/2008 | Liebschner |
| 7,917,201 B2 | 3/2011 | Gozani et al. |
| 8,157,731 B2 | 4/2012 | Teller et al. |
| 8,226,579 B2 | 7/2012 | Barlow et al. |
| 8,251,926 B2 | 8/2012 | Barlow et al. |
| 2004/0019382 A1 | 1/2004 | Amirouche et al. |
| 2006/0074354 A1 | 4/2006 | Barlow et al. |
| 2006/0079814 A1 | 4/2006 | Barlow et al. |
| 2009/0156967 A1 | 6/2009 | Cohen |
| 2009/0222214 A1 | 9/2009 | Barlow et al. |
| 2010/0075285 A1 | 3/2010 | Stalling et al. |
| 2011/0060252 A1 | 3/2011 | Simonsen et al. |

FOREIGN PATENT DOCUMENTS

| | | |
|---|---|---|
| GB | 1206014 A | 9/1970 |
| WO | 2006026623 A2 | 3/2006 |
| WO | 2006081376 A1 | 8/2006 |
| WO | 2008067607 A1 | 6/2008 |

OTHER PUBLICATIONS

Barlow et al, "Mechanically evoked perioral reflexes in infants." Brain Res., 1992, pp. 158-160, vol. 599, No. 1.

Finan et al, "The actifier: a device for neurophysiological studies of orofacial control in human infants." J Speech Hear Res, 1996, pp. 833-838, vol. 39, No. 4.

Chinese Applicaiton Serial No. 200910008046.7, Response filed Apr. 28, 2012 to Office Action mailed Dec. 13, 2011, 4 pgs.

Chinese Application Serial No. 200910008046.7, Office Action mailed Dec. 13, 2011, 5 pgs.

European Application Serial No. 09250464.6, Office Action mailed Mar. 22, 2012, 11 pgs.

Estep et al., "Non-Nutritive Suck Parameter in Preterm Infants with RDS." J Neonatal Nurs, 2008, pp. 28-34, vol. 14, No. 1.

Poore et al., "Respiratory treatment history predicts suck pattern stability in preterm infants." J Neonatal Nurs, 2008, pp. 185-192, vol. 14, No. 6.

Popescu et al., "Non-nutritive sucking recorded in utero via fetal magnetography." Physiol Meas, 2008, pp. 127-139, vol. 29, No. 1.

Stumm et al., "Respiratory Distress Syndrome Degrades the Fine Structure of the Non-Nutritive Suck in Preterm Infants." J Neonatal Nurs, 2008, pp. 9-16, vol. 14, No. 1.

Vantipalli et al.; Somatosensory entrainment of suck in preterm infants: NTrainer CNL Technical Research Report; 2006; 3:1-23 entire document.

Goldfield et al.; "Coordination of Sucking, Swallowing, and Breathing and Oxygen Saturation During Early Infant Breast-feeding and Bottle-feeding"; Pediatric Research; vol. 60; No. 4; pp. 450-455; Oct. 2006.

PCT/US2013/038405 International Search Report and Written Opinion mailed Jul. 11, 2013; (10 pages).

PCT/US2013/038410 International Search Report and Written Opinion mailed Jul. 15, 2013 (8 pages).

PCT/US13/38400 International Search Report and Written Opinion mailed Jul. 19, 2013 (15 pages).

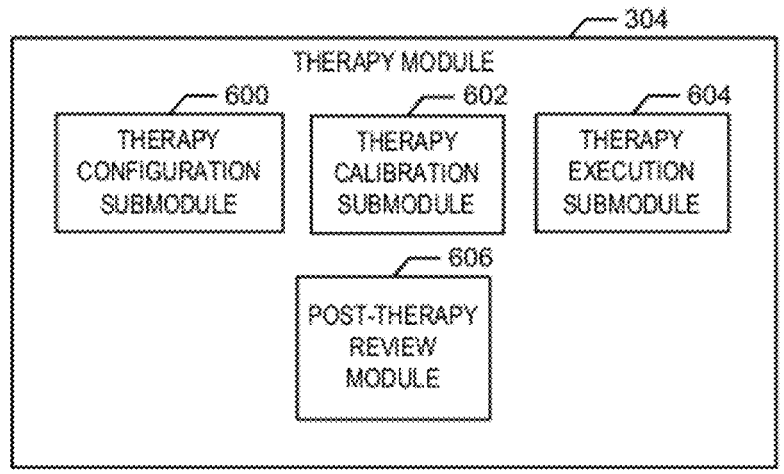
FIG. 6
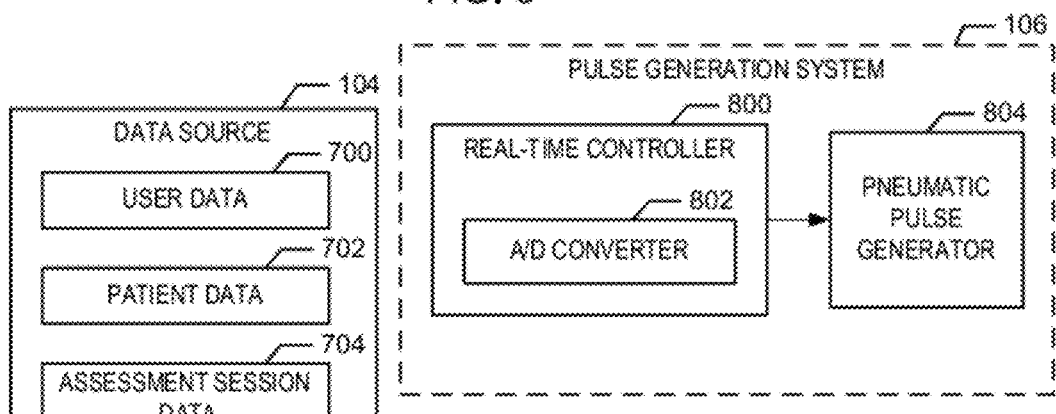
FIG. 7
FIG. 8
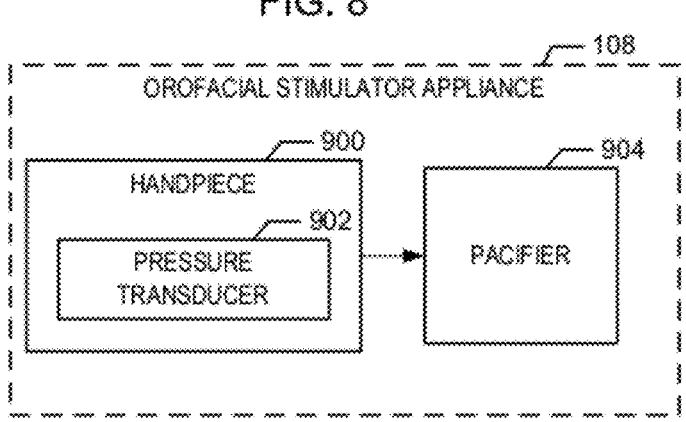
FIG. 9

Please describe the dominant patient state for the session

Patient State: No Value

Please verify that the completed assessment is assigned to the correct patient

● correct, assigned to patient: Simpson, Homer

○ incorrect, reassign to patient

Add optional notes

FIG. 26

ENHANCED THERAPEUTIC STIMULUS FOR NON-NUTRITIVE SUCK ENTRAINMENT SYSTEM AND METHOD

CROSS REFERENCE TO RELATED APPLICATIONS

This application is a continuation-in-part of U.S. patent application Ser. No. 12/390,142, entitled "Method and Apparatus for Measuring Non-Nutritive Suck Pattern Stability" filed on Feb. 20, 2009, which claims priority to U.S. Provisional Application No. 61/036,304 filed on Mar. 13, 2008 and U.S. Provisional Application No. 61/030,484 filed on Feb. 21, 2008, all of which are incorporated by reference in their entireties.

FEDERALLY SPONSORED RESEARCH OR DEVELOPMENT

This subject matter discussed in this patent application was funded in part by United States Grant No. R01-DC003311 from the National Institute of Health (NIH). The government may have certain rights to the subject matter discussed herein.

FIELD OF THE INVENTION

The invention relates generally to a software system and processing devices or appliances incorporating the software system to assess the organization of a non-nutritive suck (NNS) pattern of a patient and to entrain an organized NNS pattern in the patient. More specifically, the present invention relates to a software system that receives data from an orofacial stimulation appliance to assess the patient's natural NNS pattern and generates a tactile stimulus via the orofacial stimulation appliance to entrain an organized NNS pattern.

BACKGROUND OF THE INVENTION

Premature birth places infants at increased risk for learning disabilities, delayed development of speech, language and motor skills, and mortality. The premature infant often has difficulties with respiration and feeding and therefore may remain in the hospital for prolonged periods of time. The non-nutritive suck (NNS) is a motor behavior which can be observed and used to make inference about brain development and organization in this young population.

Oral stimulation therapy is a common practice, in which feeding therapists manually apply a stimulation using their fingertip. Manually applying stimulation, however, has a number of drawbacks. One such drawback includes the variance and limitation in the amount of motion (amplitude) and rhythm (frequency) from therapist to therapist, or even by the same individual. As a result, extensive and costly training and experience are required for a therapist to be proficient at providing manual stimulation and assessment.

In addition, manual stimulation is given essentially blind, as patients can respond by producing a variety of undesirable motor actions, including but not limited to clenching the jaws, tongue compression, tongue thrusting, or other reactions that may be confused with desirable NNS events. As such, it can be difficult to determine if the manual stimulation is beneficial to the patient.

Therefore, a need exists for an automated system and method to assess a patient's natural NNS pattern and to provide precise and beneficial tactile stimulus to correct and organize the patients NNS pattern.

SUMMARY OF THE INVENTION

The present invention relates to a system and method for assessing and entraining a non-nutritive suck (NNS) pattern in a patient. In one aspect, the system is executable by a processor for stimulating a central pattern generator and a trigeminal nerve in a human brain, where such stimulation influences brain response or development including repair, control of respiration, control of NNS, mastication, and combinations thereof, in a human brain. The system includes an assessment module to record a pressure signal received from a pressure transducer in an orofacial stimulator appliance and generate a display signal to display assessment data based on the received pressure signal. The system also includes a feature extraction module to identify one or more components of a patient's non-nutritive suck pattern in the pressure signal, determine a symmetry of the patient's non-nutritive suck pattern, determine a repetition of the patient's non-nutritive suck pattern, and assign a spatiotemporal index value to the patient's non-nutritive suck pattern, the spatiotemporal index value indicating an overall rating of the patient's non-nutritive suck pattern.

The system further includes a therapy module to generate a therapeutic pressure pulse signal comprising a base frequency signal further comprising two or more pressure pulses, wherein each pulse period consists of a positive and negative displacement contacted by the lip and the mouth of the patient. Pulses are administered in a series of two or more pulses, and each of the two or more pressure pulses has a damped harmonic oscillating square wave profile and are separated by an interval between 500 milliseconds and 650 milliseconds in duration. The therapy module also generates a therapeutic pressure profile signal comprising at least one of the therapeutic pressure pulse signals and transmits the therapeutic pressure pulse profile signal to the orofacial stimulator appliance.

In various aspects, the base frequency is between 1.5 Hz and 5 Hz and the two or more pressure pulses causes surface motion of between about 260 microns and 300 microns, with a maximum transition interval of 20 milliseconds to 50 milliseconds. The therapeutic pressure profile may include at least 6 pressure pulses in succession contacted with the patient for at least two minutes, at least twice a day. Further, each of the two or more pressure pulse is composed of higher order harmonics of the base frequency and each pressure pulse has a square wave peak.

In other aspects, the amplitude of the higher order harmonic decay is greatest at a beginning of each pressure pulse and the higher order harmonic decay for the two or more pressure pulses vary in amplitude and a frequency. Further, in one aspect, the higher order harmonic decay for the two or more pressure pulses are identical in amplitude and a frequency. Each of the two or more pressure pulses may have a first order damped overshoot square wave profile, wherein the damped overshoot square wave profile of the two or more pressure pulses has a Q factor greater than or equal to ½. The pressure transducer generates an analog pressure signal in response to pressure applied to the orofacial stimulator appliance.

In one aspect, the display signal contains waveform data, wherein the waveform data indicates at least one event in the pressure signal. Further, the signal may contain at least one event. An event may be a pressure peak, a non-nutritive suck event, a burst, a chew, or combinations thereof. NNS values assigned to the waveform data may be based upon a suck symmetry, a suck quantity, a suck magnitude, and a burst timing of the patient's non-nutritive suck pattern. A spatiotemporal index value may be calculated that relates to the regularity of repetitive suck burst. For example, the spatiotemporal index value may measure the similarity in up to five repetitive suck bursts detected within an assessment as a measure of the reproducibility of the infant's suck.

In one aspect, the system further includes a calibration module to calibrate the orofacial stimulator appliance. The orofacial stimulator appliance is calibrated prior to receiving pressure signals at the assessment module, generating the therapeutic pressure pulse signal, or both. Alternately, the orofacial stimulator appliance may be calibrated after receiving pressure signals at the assessment module, generating the therapeutic pressure pulse signal, or both. Further, the orofacial stimulator appliance may be calibrated prior to and after receiving pressure signals at the assessment module, generating the therapeutic pressure pulse signal, or both. For example, the calibration module may verify the expansion characteristics of the pacifier. Verification is performed by measuring the frequency and amplitude of changes in the pacifier by a laser micrometer in communication with the system. The system may then digitize and record the frequency and amplitude of changes in the pacifier shape to verify that the desired therapy pulse is applied. In various other aspects, the system further includes a review module to review at least one of the assessment data, the generated therapeutic pressure profile, or both.

In various other embodiments, the system may be encoded on a non-transitory computer readable medium that is further encoded with instructions for operating a non-nutritive system for generating non-nutritive stimulus for a patient. The instructions are executable by a processor in communication with memory. The present invention also relates methods of using the software system. Related objects and advantages of the present invention will be apparent from the following description.

DESCRIPTION OF FIGURES

FIG. 6 is a block diagram of an assessment module according to one aspect of the non-nutritive suck assessment and entrainment system.

FIG. 7 is a block diagram of a therapy module according to one aspect of the non-nutritive suck assessment and entrainment system.

FIG. 8 is a block diagram of a therapeutic pulse generation system according to one aspect of the non-nutritive suck assessment and entrainment system.

FIG. 9 is a block diagram of an orofacial stimulator appliance according to one aspect of the non-nutritive suck assessment and entrainment system.

FIGS. 12-31 are screenshots of various graphic user interface displays according to aspects of the non-nutritive suck assessment and entrainment system.

DETAILED DESCRIPTION OF THE INVENTION

The present invention relates to a system for assessing and the neural entrainment of a Non-Nutritive Suck (NNS) pattern in a patient. Typically, the patient is a premature infant; however, the system may also be used for patients unable to properly suck or swallow to receive nourishment, including but not limited to full-term infants, toddlers, adolescents, and adults. For example, the system may be used to treat those that have been debilitated by strokes, hemorrhages, or other conditions that correlate with an impairment in neurological development or function.

The NNS pattern of a patient is generated by the patient's suck central pattern generator (sCPG). A central pattern generator (CPGs) is a neural circuit or combination of neural circuits located in the patient's cerebral cortex, brainstem, and/or spinal cord that drives rhythmic motor behaviors such as sucking, breathing, mastication, and locomotion. The patterns generated by the CPGs can be modulated by a variety of external stimuli. As such, the most beneficial therapeutic results are manifested when the therapy consistently mimics the intrinsic frequency of sCPG.

It is often difficult for therapists to model the fine temporal structure of an organized NNS burst pattern, which involves a frequency-modulated (FM) burst structure, using manual stimulation. The FM burst structure is characterized by a series of suck cycles that successively decrease in frequency from the first compression cycle of the lips and mouth to the last compression cycle. The FM burst structure typically modulates between 1.5 Hz and 3 Hz. The structure of the FM burst is very difficult if not impossible to produce manually in a repeated pattern by even the most experienced therapist.

The present invention relates to the identification of particular characteristics of the FM burst structure and provides criteria or descriptions of features of the NNS pattern that may be used as diagnostic indicators for gauging the development of oromotor control among patients. Further, the identified characteristics may be useful in configuring a tactile stimulus that may be applied to patients to modify or correct a deficient NNS pattern.

Figure 1:
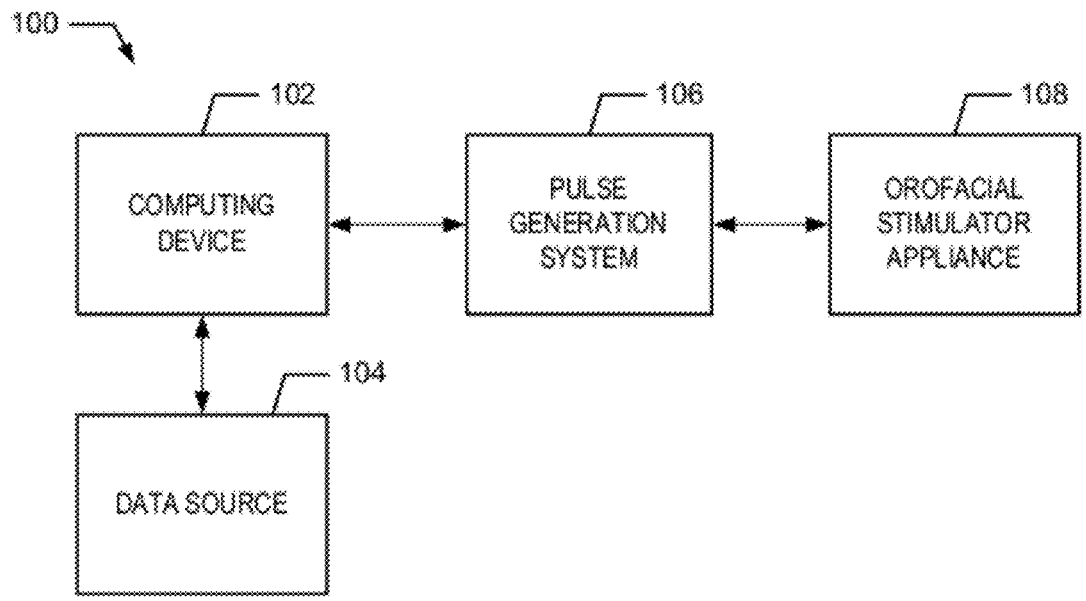
FIG. 1 is a block diagram of a non-nutritive suck assessment and entrainment system according to one aspect.

FIG. 1 is a block diagram of a non-nutritive suck (NNS) assessment and entrainment system (NNS system) 100 for assessing a patient's natural NNS pattern and for providing a tactile stimulus that will stimulate the suck central pattern generator (sCPG) and trigeminal nerve of a human brain to entrain a proper NNS pattern. Further, the NNS system 100 may be used to assess and entrain brain activity for controlling respiration, mastication, or combinations thereof. The NNS system 100 includes a computing device 102 to process data and execute one or more applications, a data source 104 to store data, a pulse generation system 106 to generate pneumatic pulses in response to input signals, and an orofacial stimulator appliance 108 to transfer the pneumatic pulses to a patient as a tactile stimulus.

Figure 2:
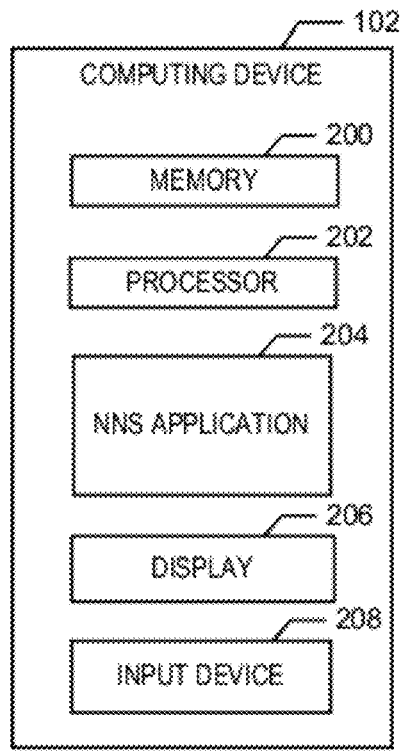
FIG. 2 is a block diagram of computing environment according to one aspect of the non-nutritive suck assessment and entrainment system.

According to one aspect, the computing device 102 includes memory 200 and at least one processor 202 to execute a NNS assessment and therapy application (NNS application) 204, as shown in FIG. 2. The computing device 102 also includes a display 206, such as a computer monitor, for displaying data stored in the data source 104, data received from the pulse generation system 106 or the orofacial stimulator appliance 108, and data input by a user of the NNS system 100. The display device 206 also displays one or more graphical user interfaces (GUIs) input forms or displays, generated by the NNS application 204, as shown in FIGS. 12-31. The GUI input forms and displays enable a user of the NNS system 100 to input, view, and/or interact with the various modules of the system. The GUI input forms and displays also allow a user to input, view, and/or interact with patient data, NNS assessment data, NNS therapy data, and/or other data related to the assessment and therapeutic stimulation of the patient. Further, the GUI input forms and displays permit a user to configure and interact with the pulse generation system 106 and the orofacial stimulator appliance 108.

The computing device 102 may also include an input device 208, such as a keyboard or a pointing device (e.g., a mouse, trackball, pen, or touch screen) to enter data or configure a feature of the NNS system 100 using the GUI input forms and displays. The computing device 102 may further include, or at least be in communication with, the data source 104.

The data source 104 may be a database stored on a local hard disk drive (HDD) incorporated into the computing device 102. Alternately, the data source 104 may be a database or other data structure stored remotely from the computing device 102. For example, the computing device 102 may be in communication with the data source 104 over a network, including but not limited to the Internet. As shown in FIG. 7, the data source may store a variety of data. For example, the data source 104 may store user data 700 that includes profiles and login information, such as passwords, for users of the NNS system 100. The data source 104 may also contain patient data 702 including patient charts and historical assessment and therapy session data 704 and 706, respectively. The data source 104 also stores data for therapy pulse profiles 708 that may be used to entrain a variety of patients, as well as, other data 710 gathered from experiments or research trials conducted using the NNS system 100.

Figure 3:
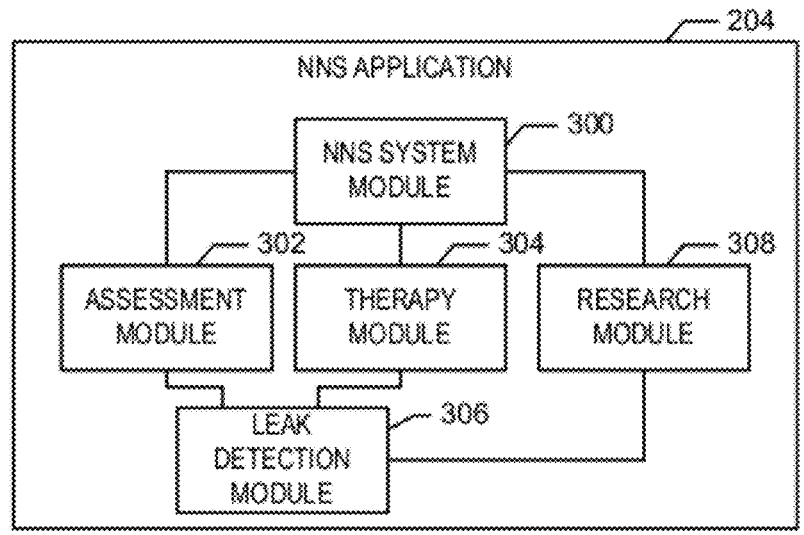
FIG. 3 is a block diagram of data source according to one aspect of the non-nutritive suck assessment and entrainment system.
Figure 4:
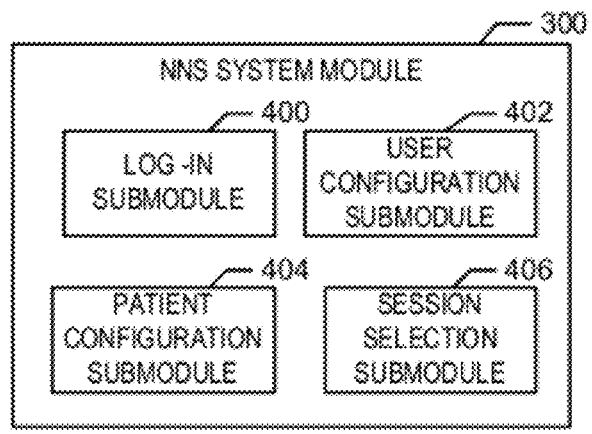
FIG. 4 is a block diagram of a non-nutritive suck entrainment application according to one aspect of the non-nutritive suck assessment and entrainment system.
Figure 5:
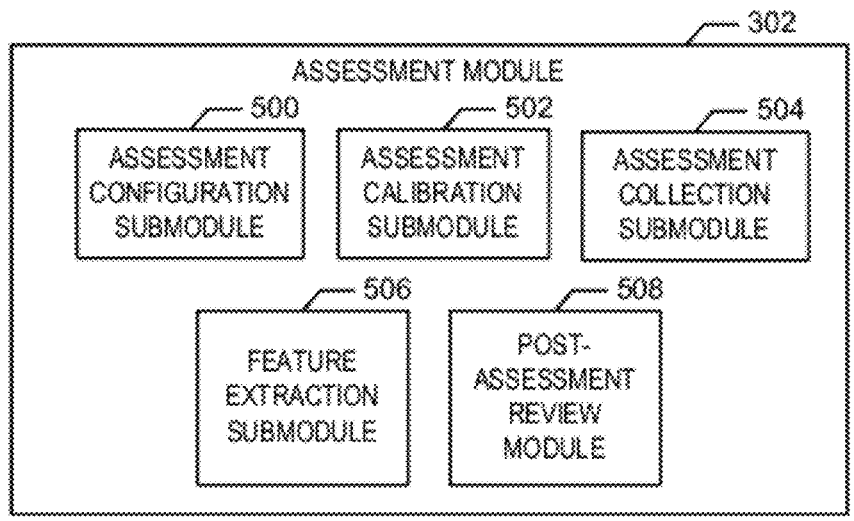
FIG. 5 is a block diagram of a system module according to one aspect of the non-nutritive suck assessment and entrainment system.

According to one aspect, as shown in FIG. 3, the NNS assessment and therapy application 204 includes a number of instructions, applets, modules 300-308, and submodules to receive, process, and generate data and/or signals for the assessment of a NNS pattern and the therapeutic stimulation of a patient's mouth and lips to entrain a proper NNS pattern. The modules of the NNS assessment and therapy application 204 include an NNS application system module 300, an assessment module 302, a therapy module 304, a leak detection module 306, and a research module 308.

Figure 12:
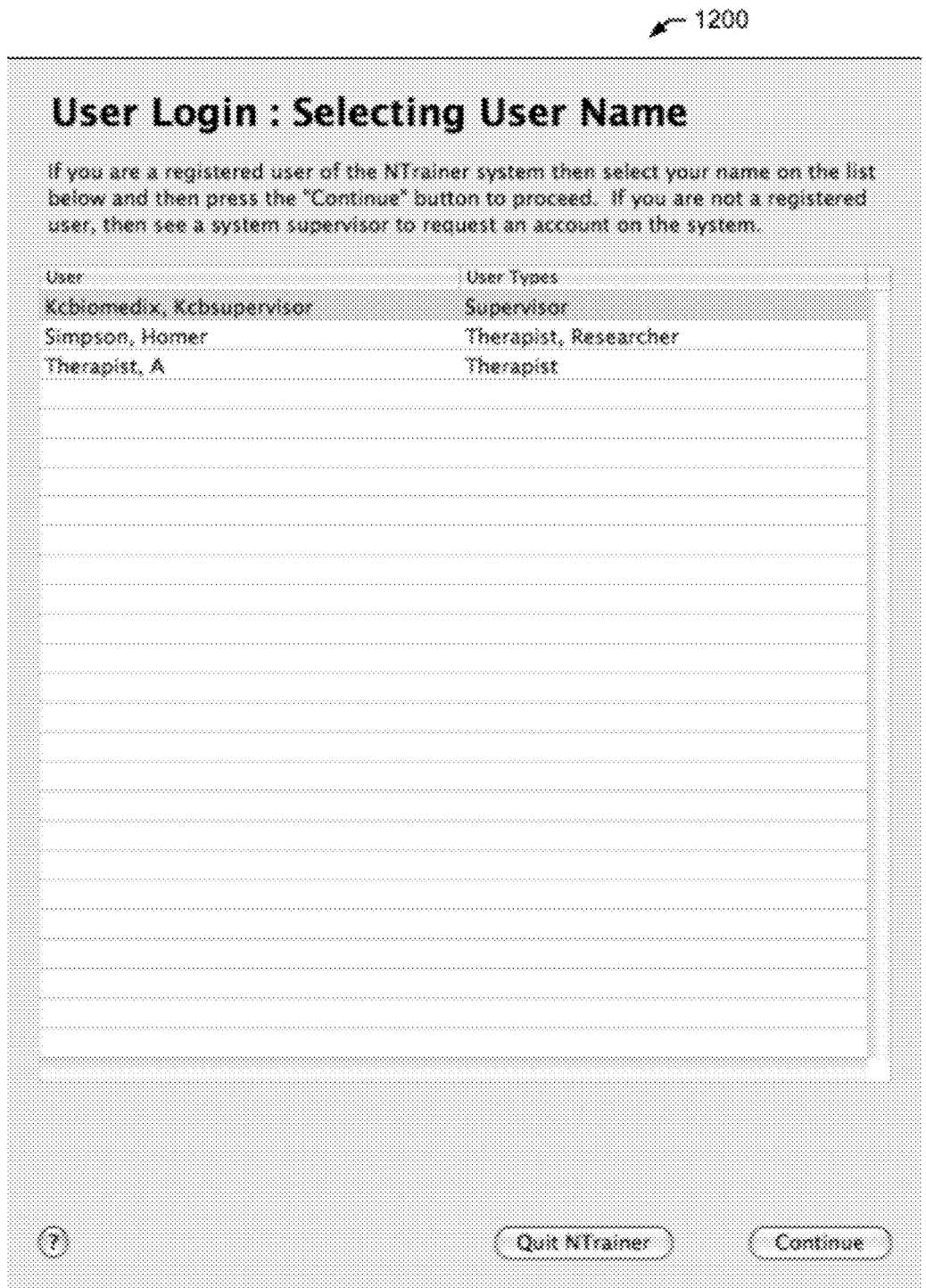
Figure 13:

The NNS application system module 300 includes various submodules 400-406 to provide access to various features and functionality of the NNS assessment and therapy application 204. For example, the NNS application system module 300 includes a user login submodule 400 that allows a user of the NNS system 100 to login into the NNS application 204. In one aspect, the NNS application system module 300 generates GUI input forms 1200 and 1202, as shown in FIGS. 12-13, where the user may select a user account and log in to the NNS application 204 after entering a valid password for the selected user.

Figure 14:
Figure 15:
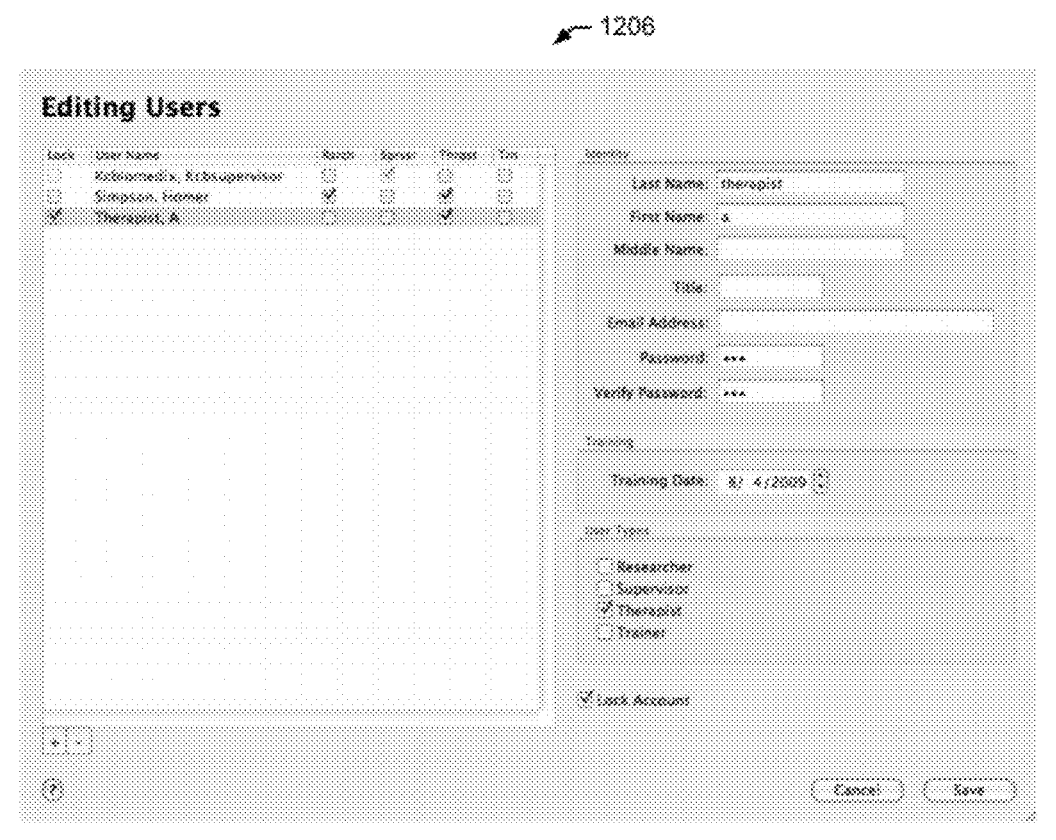
Figure 19:
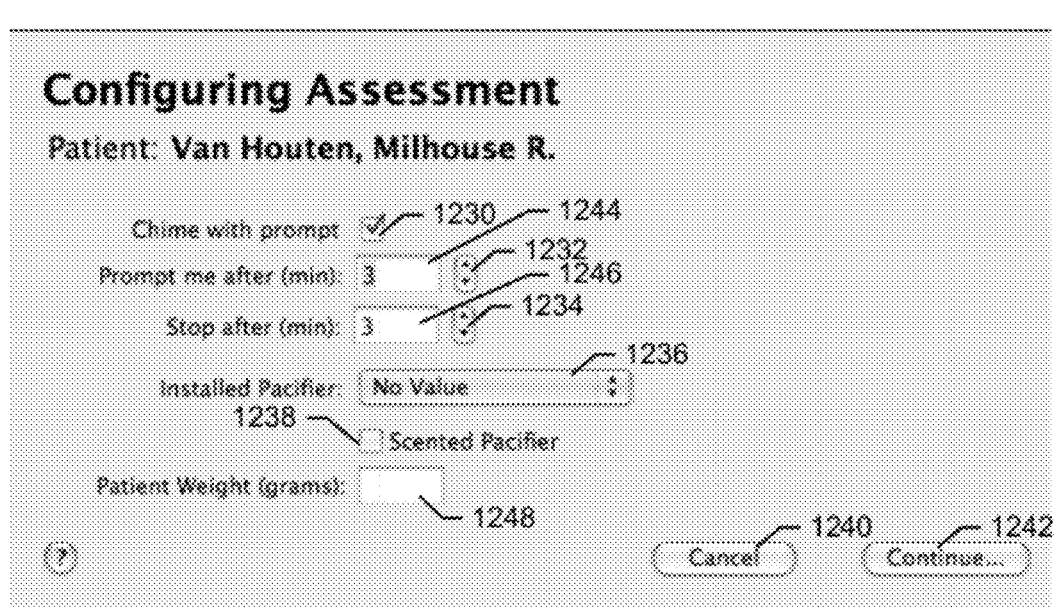
Figure 20:
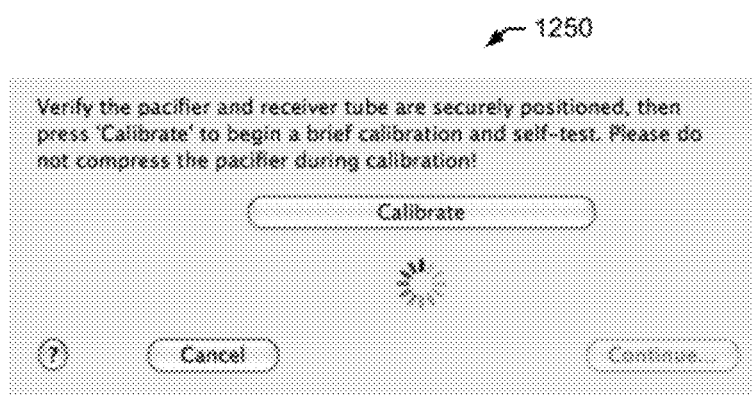
Figure 21:
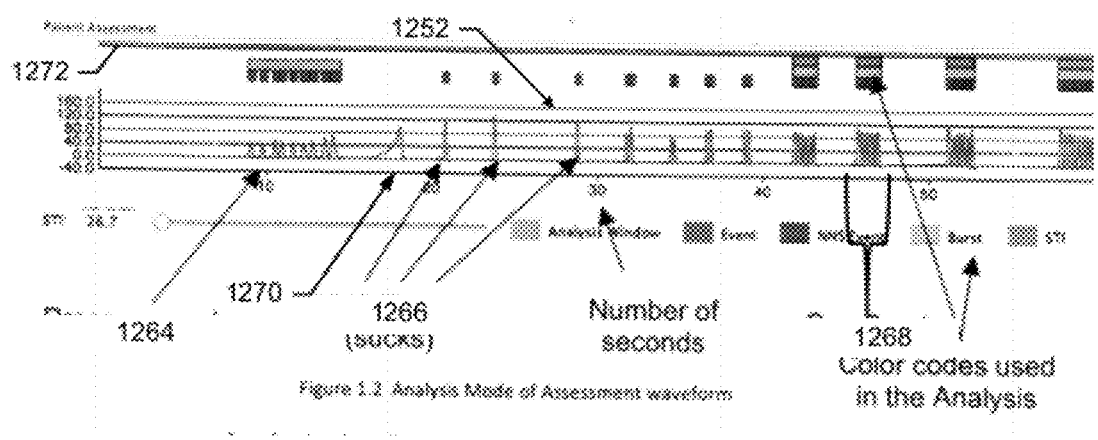
Figure 22:
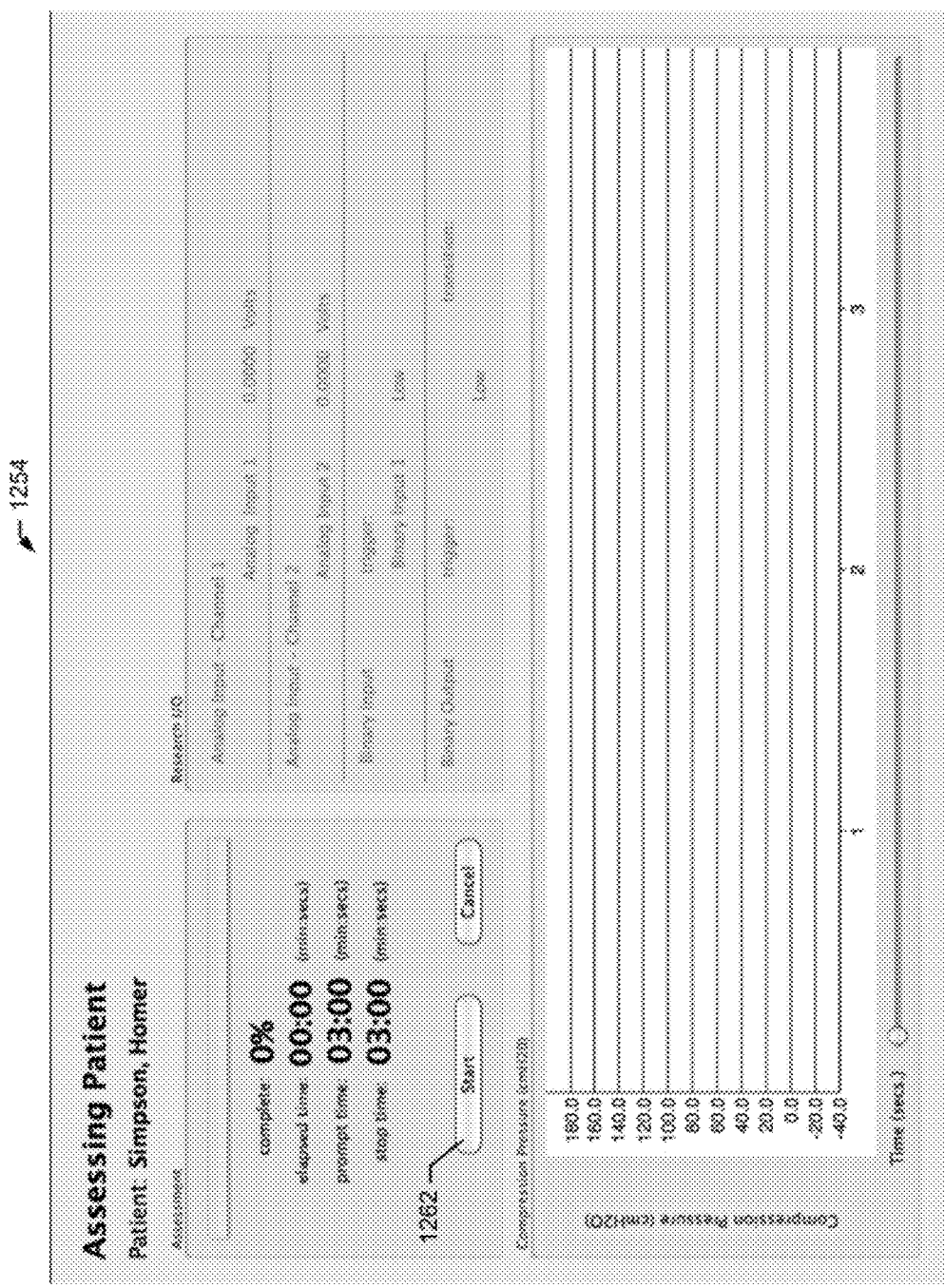
Figure 23:
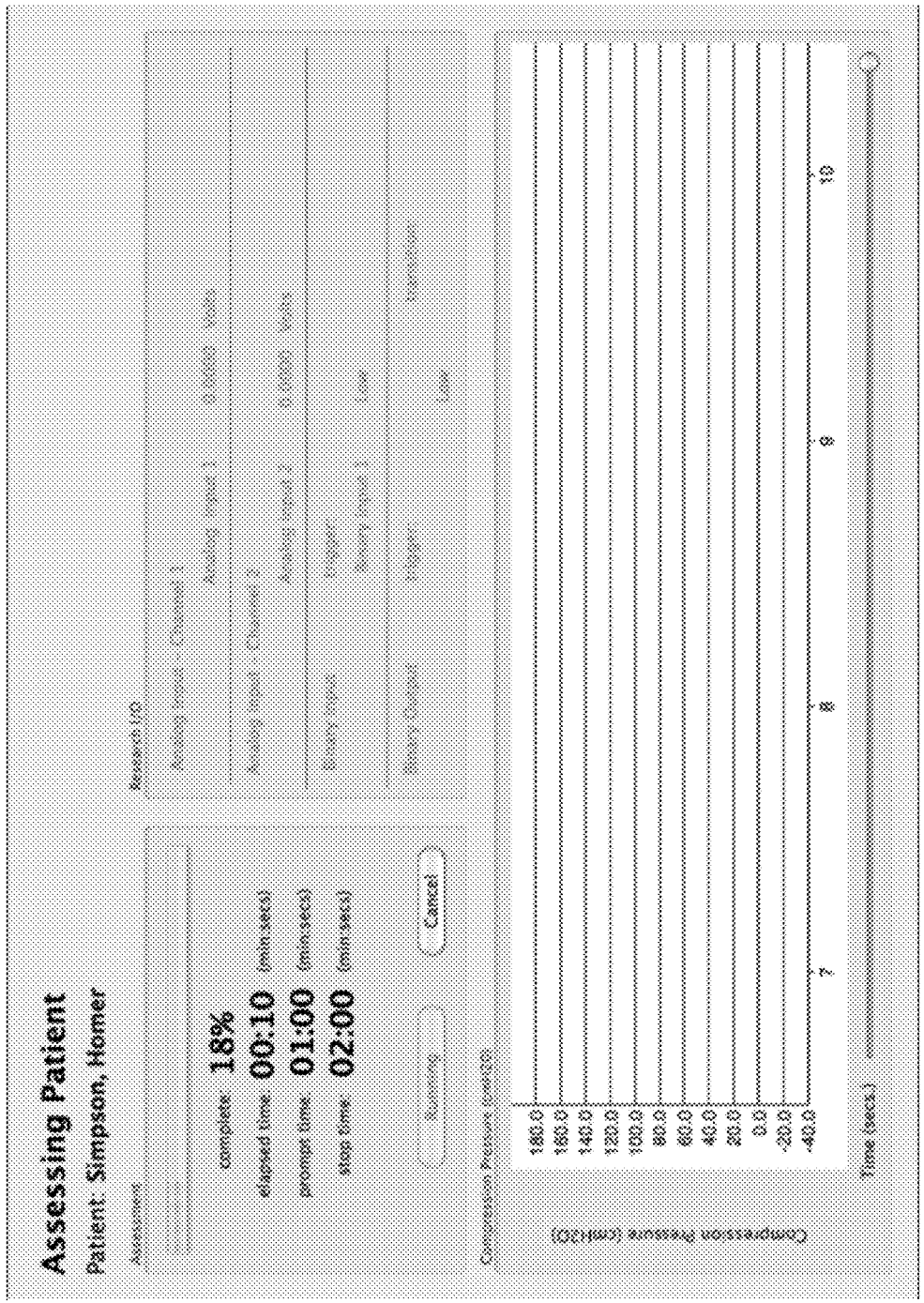
Figure 24:
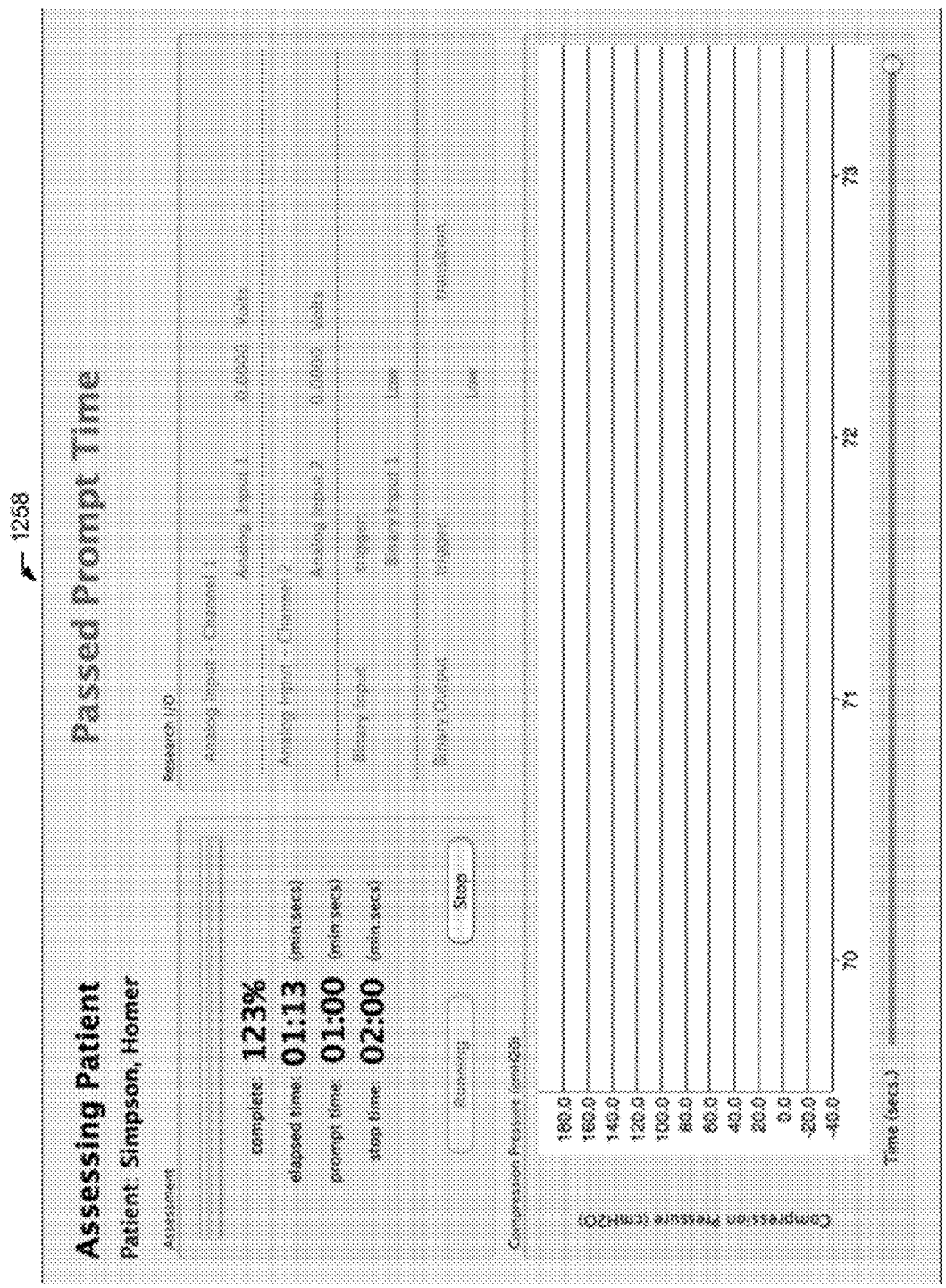
Figure 25:
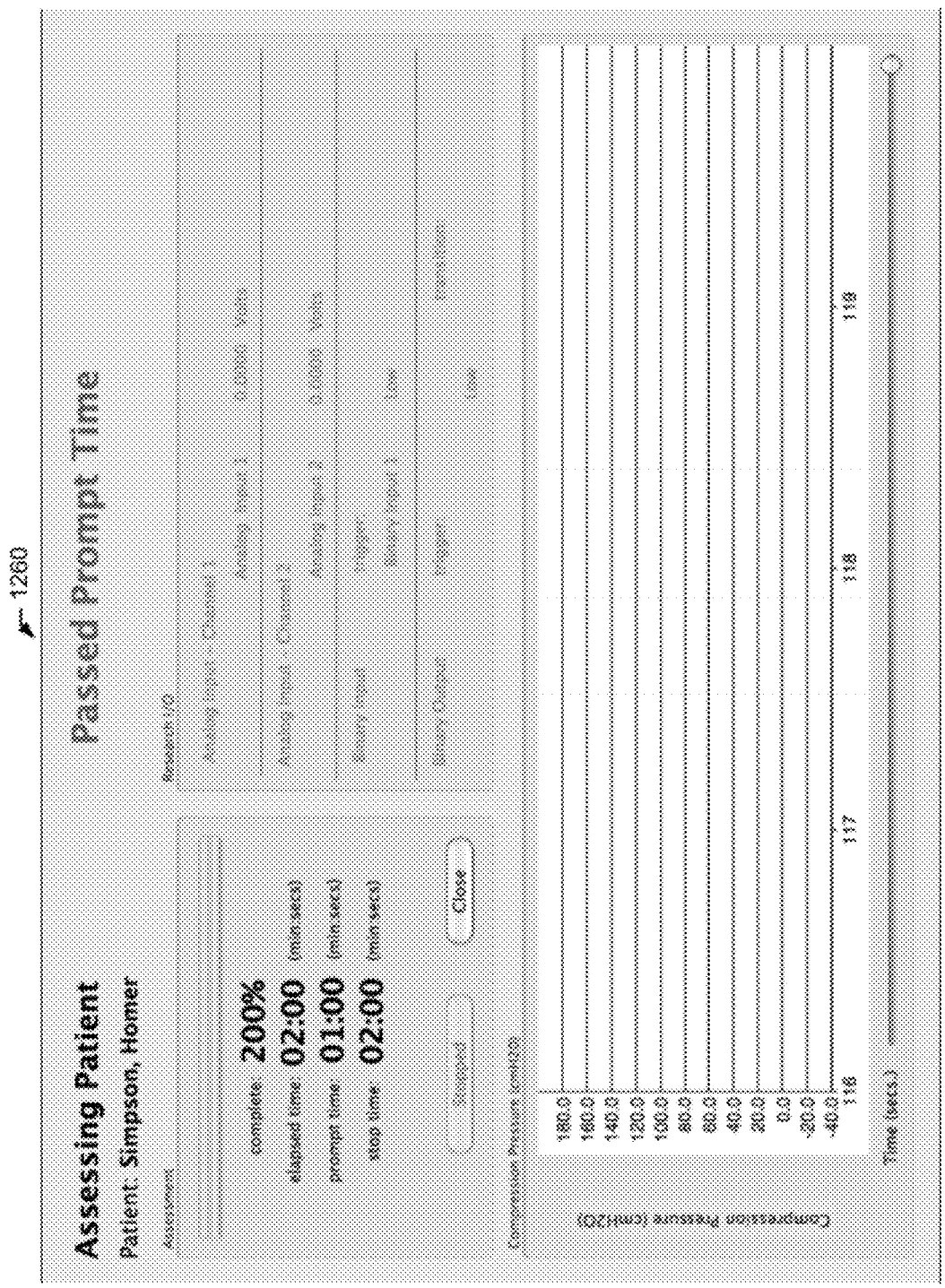

The NNS application system module 300 includes a user configuration submodule 402 that allows users of the NNS system 100 with sufficient privileges to add, edit, or delete user accounts. By way of example and not limitation, an administrator may input data into GUI input forms 1204 and 1206, as shown in FIGS. 14-15 to create, modify, or delete a user profile to grant or restrict access to the NNS application 204.

Figure 16:
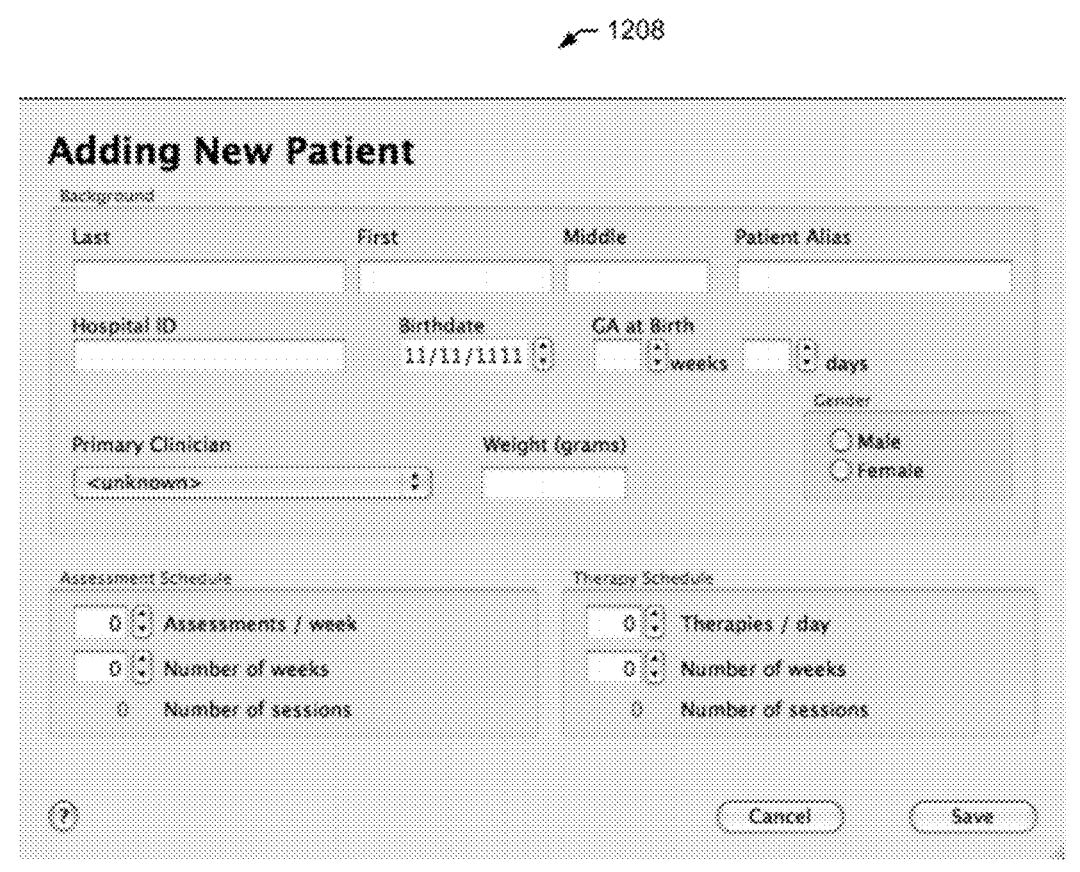
Figure 17:
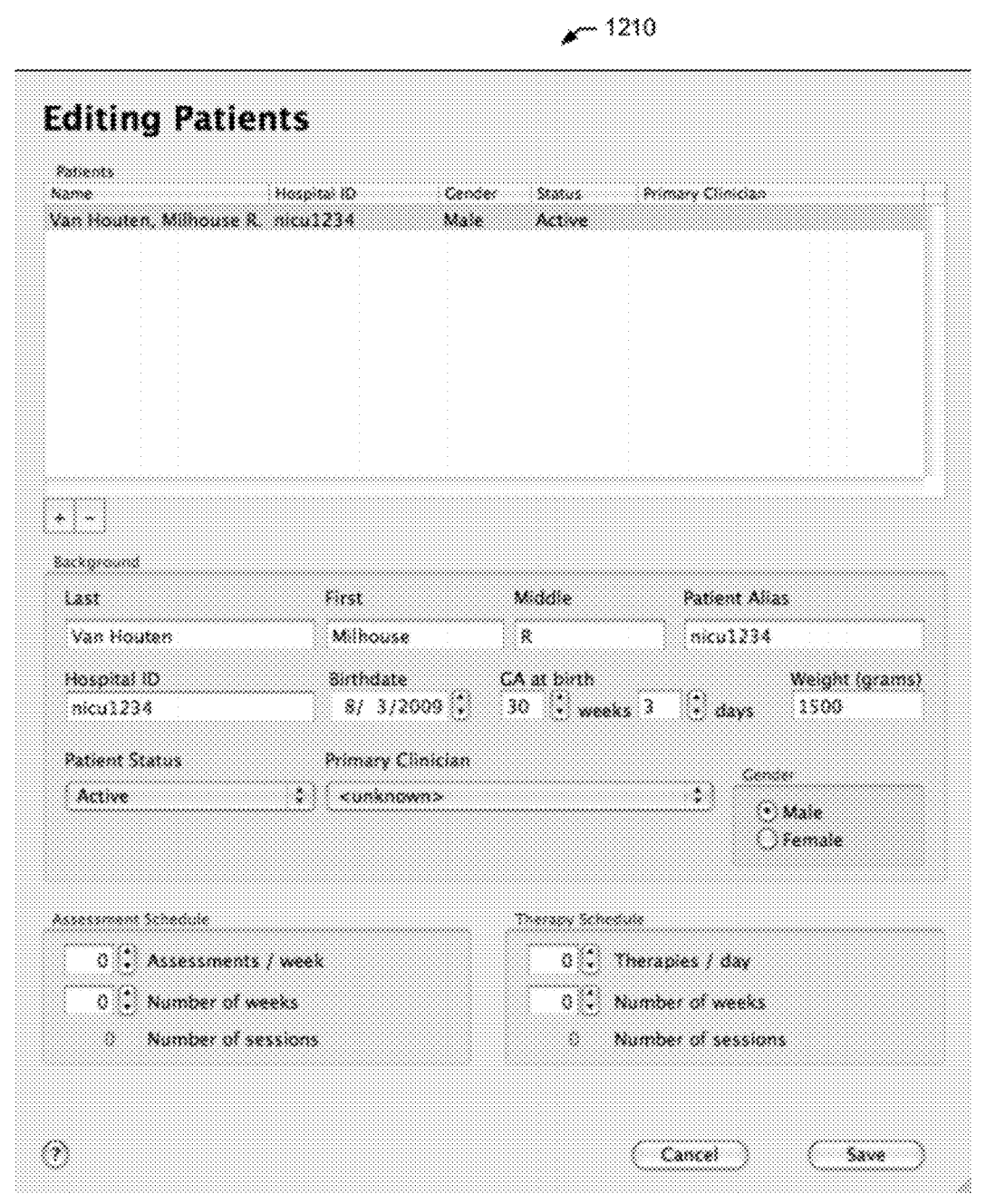

Similarly, the NNS application system module 300 includes a patient configuration submodule 404 that allows users of the NNS system 100 with sufficient privileges to add, edit, or delete patients. By way of example and not limitation, an administrator may input data into input forms 1208 and 1210, as shown in FIGS. 16-17, to create, modify, or delete a profile for a patient that may receive an NNS assessment or therapy using the NNS system 100. The NNS application system module 300 also includes a session selection submodule 406 that allows users of the NNS system 100 to select whether the NNS system will be used to assess a patient's naturally generated NNS pattern or to provide therapeutic stimulus to the patient. As such, the session selection submodule 406 sends requests to the assessment module 302 and the therapy module 404 in response to type of session selected by the user.

Figure 18:
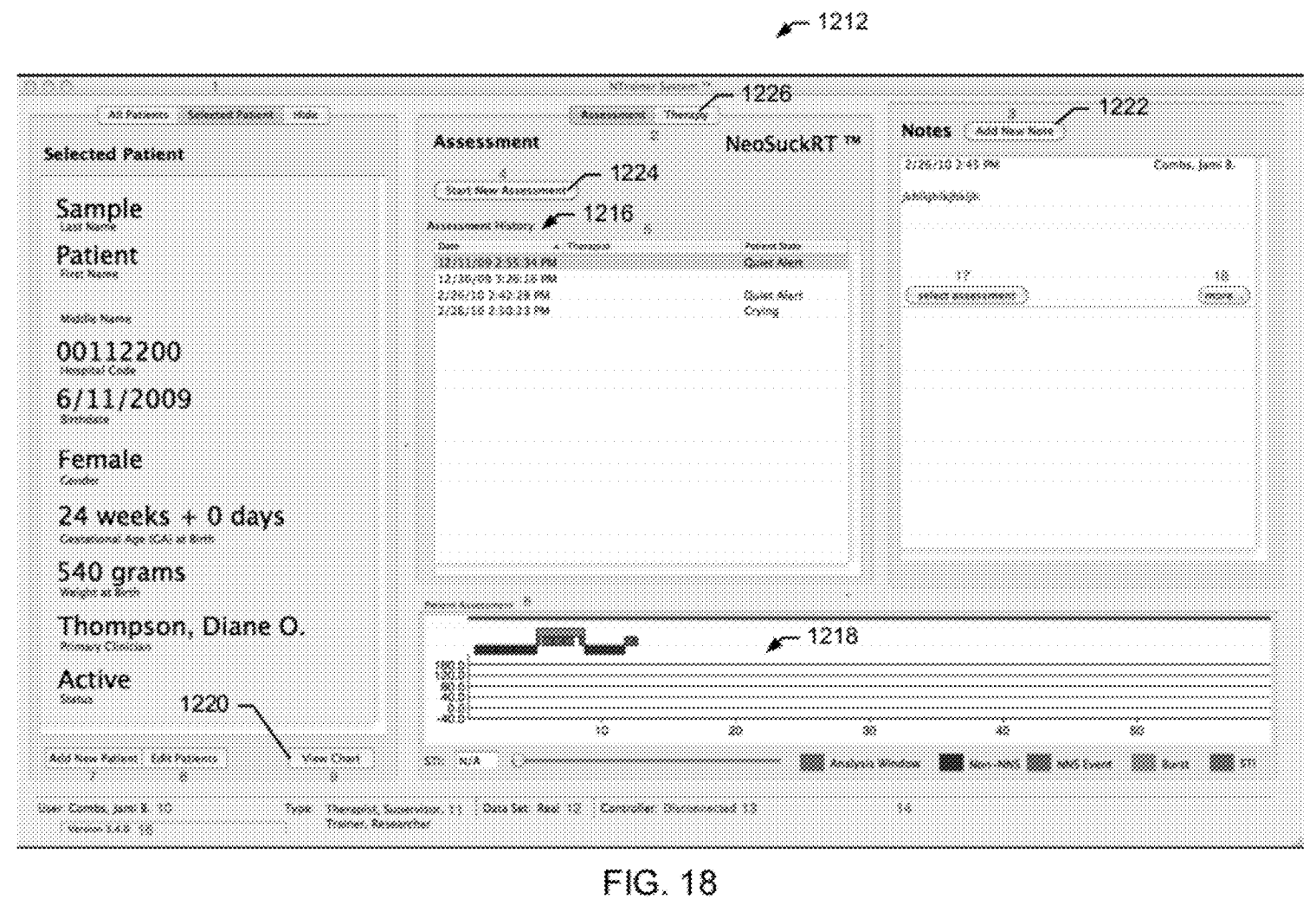

When an assessment request is generated, the NNS application system module 300 generates a main assessment input form 1212 to allow the user to input data and interact with the NNS application 204 during the assessment session. By way of example, and not limitation, an embodiment of the main assessment input form 1212 is shown in FIG. 18. In one aspect, the main assessment input form 1212 includes one or more control buttons 1214 to access a list of all the patients actively associated with the NNS application 204. When a patient is selected, the main assessment input form 1212 displays a history 1216 of assessments for the selected patient, and is capable of displaying waveforms from the previous assessments in a waveform frame 1218. In one aspect, the prior waveforms and assessment histories 1216 may be stored as assessment session data 704 in the data source 104.

Figure 31:
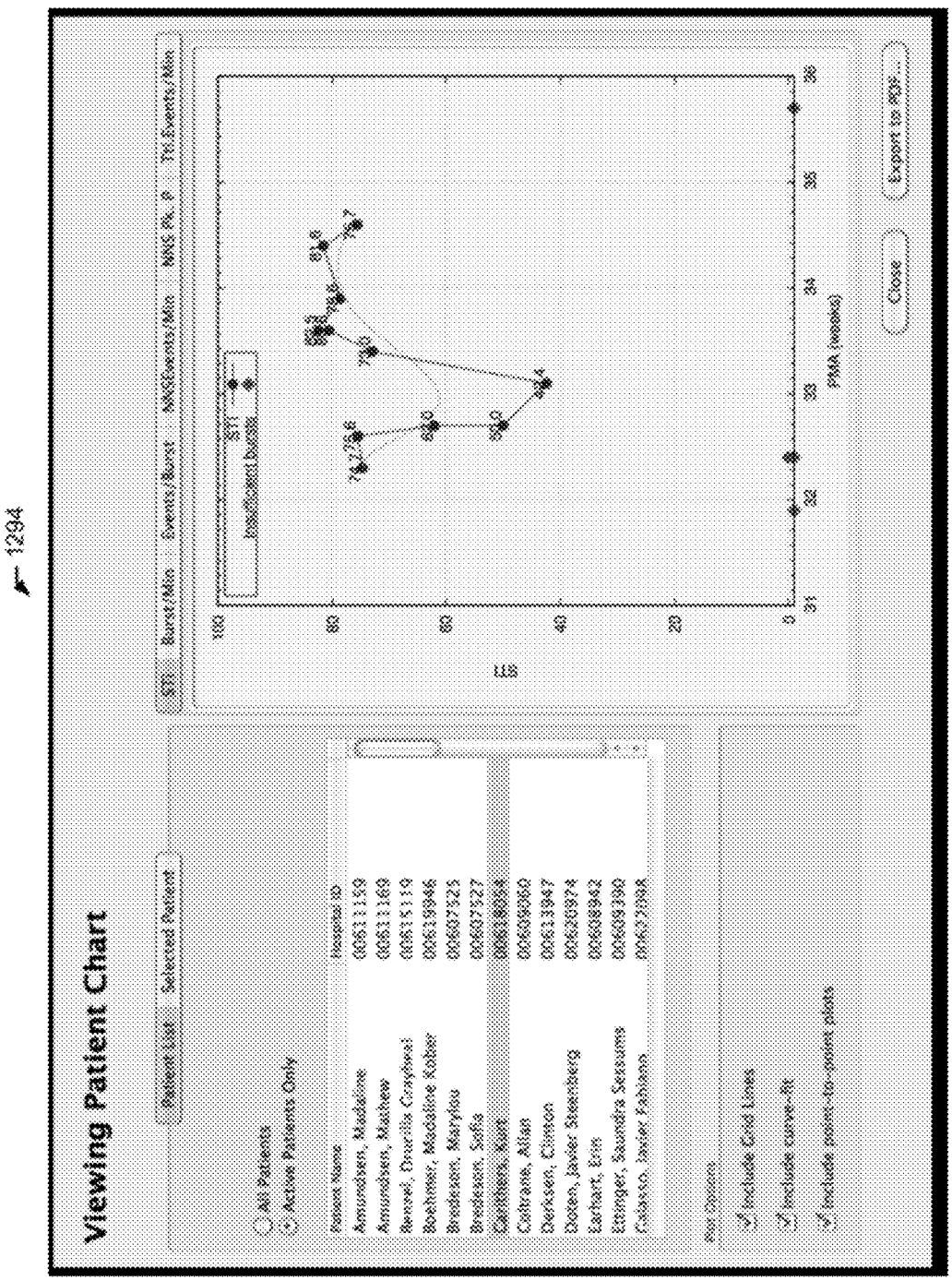

The main assessment input form 1212 also includes a control button 1220 to permit a user to view a patient's medical chart 1294, an example of which is shown in FIG. 31. In addition, the control button 1220 allows the user to add or edit patient data, while control button 1222 allows the user to add notes to the patient assessment data. In addition, the user may select control button 1224 to start a new assessment session for the selected patient or select control button 1226 to switch directly to a therapy session for the selected patient.

In one aspect, an assessment session consists of recording and displaying a signal received at the computing device 102 from a pressure transducer 902 of the orofacial stimulator appliance 108, as shown in FIG. 9. The transducer 902 translates pressure changes caused by sucking and mouthing movements of the patient into an analog signal that tracks the pressure applied to a pacifier 904 versus time. The analog pressure signal is converted to a digital signal at an analog-to-digital converter 802 of the pulse generation system 106. The analog-to-digital converter 802 is incorporated into a real-time controller 800, that receives and modifies received and/or generated pressure signals in real-time. The digital pressure signal is then received, recorded, and displayed by the assessment module 302.

In one aspect, the assessment module 302 includes a number of submodules 500-508, including but not limited to an assessment configuration submodule 500, an assessment calibration submodule 502, an assessment capture module 504, a feature extraction submodule 506, and a post assessment review module 508. The various submodules 500-58 generate and display one or more GUI input forms as shown in FIGS. 19-26 that allow the user to configure, initiate, and review an assessment session.

The assessment configuration submodule 500, for example, generates an assessment configuration GUI input form 1228. The assessment configuration GUI input form 1228 includes one or more controls 1230-1242 and data fields 1244-1248 to input data related to a total assessment time 1246, an intermediate assessment prompt 1244, a type and configuration 1236 of the pacifier 904, and optionally, the patient's weight 1248. As the behavior and mood of a patient is often unpredictable, it's difficult for the user to know in advance how long the assessment session may take. Therefore, the intermediate assessment prompt is selected as a 'best estimate' for the actual time that it may take to capture enough NNS pattern activity to assess the patient. As such, the total assessment time permits the user to continue to collect data, if desired, after intermediate assessment prompt. In one aspect, the assessment collection submodule 504 halts the capture of assessment data at the intermediate assessment prompt.

The assessment calibration submodule 502 generates an assessment calibration GUI input form 1250. In one aspect, the calibration input form 1250 allows the user to communicate with and configure the pulse generation system 106 and the orofacial stimulator appliance 108 to verify the intended function and calibration for the components of the pulse generation system and the orofacial stimulator appliance prior to the initiation of an assessment session.

The assessment capture submodule 504 receives the digital pressure signal from the pulse generation system 106. In one aspect, the assessment capture submodule 504 records and displays the patient's NNS pattern activity as a waveform 1252. In other aspects, the assessment capture submodule 504 may receive and store the digital pressure signal without displaying the NNS pattern activity. In another aspect, the assessment capture submodule 504 may display the NNS pattern activity in another form, such as a chart, graph, or table.

The assessment capture submodule 504 may further generate a number of displays during the assessment capture session. For example, FIGS. 22-25 are screen displays that show the progress of the assessment session at the start of the session 1254, at the intermediate prompt interval 1256, at the user input duration time 1258, and at the conclusion of the assessment session 1260. In other aspects, fewer or a greater number of displays 1254-1260 may be provided during the assessment session.

In one aspect, the assessment data capture session may be initiated by input received through a start control button 1262 shown on the display 206. Alternately, the assessment data capture session may be initiated by a switch on a handpiece 900 of the orofacial stimulator appliance 108.

During or subsequent to an assessment session, the feature extraction submodule 506 analyzes the digital pressure signal received by the assessment capture submodule 504. In particular, the feature extraction submodule 506 identifies various components of the patient's generated NNS pattern. For example, in the waveform 1252 of FIG. 21, the feature extraction submodule 506 identifies pressure peaks 1264, individual suck events 1266, as well as bursts 1268, which are defined as two or more suck events in less than about 1.2 seconds. In addition, the feature extraction submodule 506 also identifies a number of non-NNS events 1270, such as chewing motions made by the patient. In one aspect, the feature extraction submodule 506 may provide annotations, including color-coding, to identify the various NNS events 1264-1268.

In one aspect, the feature extraction submodule 506 quantifies the overall performance of the patient's generated NNS pattern by assigning a Spatiotemporal Index (STI) value to the pattern. For example, the STI value may be derived by calculating the similarity of up to five individual suck bursts. The STI value measures the symmetrical and repetition of the patient's generated NNS burst pattern by integrating the symmetry and quantity of selected NNS events 1264-1268 in the patient's NNS pattern.

In another aspect, the feature extraction submodule 506 automatically determines a number of parameters that are desirable for evaluating the patient's generated NNS pattern and determining the best course of therapy to treat the patient. For example, the evaluation parameters may include the STI value for the waveform, the number of bursts per minute, the number of events per burst, the number of NNS events per minute, an average peak pressure, as well as the total number of events per minute. In other examples, a fewer or greater number of parameters as well as different parameters may be considered when evaluating the patient's generated NNS pattern.

The evaluation parameters may be determined using a portion or subset of the collected assessment data. For example, a "most active" two-minute window having the most number of NNS events is identified by the feature extraction submodule 506. The most-active window is generally indicated by a bar 1272 on the displayed waveform 1252. When calculating the six evaluation parameters, the feature extraction submodule 506 may ignore any NNS activity outside of the most-active window.

After capturing the patient's generated NNS pattern and determining the evaluation parameters, the post assessment review module 508 generates a post-session GUI input form 1274 where the user may confirm the identify of the patient that underwent the assessment session and input notes regarding the assessment session. By way of example and not limitation, the user may indicate the state of alertness for the patient, by inputting terms such as alert, crying, drowsy, sleepy, or any other term that identifies the patient's level of alertness during the assessment session. The user may further quantify the patient's state of alertness as active or quiet, as the patient's STI value may fluctuate between assessment sessions due to the patient drifting off to sleep during the capture period.

Once a patient has been diagnosed or characterized as having a disorganized NNS pattern, it is often desirable for the patient to undergo a therapy session to entrain the patient's sCPG to produce an organized NNS pattern. Typically, a therapy session consists of applying an external stimulus to or near the lips and mouth of the patient in order to modify the NNS pattern generated by the sCPG. The orofacial stimulator appliance 108 contacts the patient on or near the lips and mouth to deliver therapeutic stimulation, provided by the pacifier's motion as caused by the pressure pulses, to the patient's orofacial nerves via regulated changes in the surface diameter of the pacifier 904. The pressure pulses conveyed by the orofacial stimulator appliance 108 are actuated at the pulse generator 104 system in response to a therapy pulse profile generated by the therapy module 304.

Figure 27:
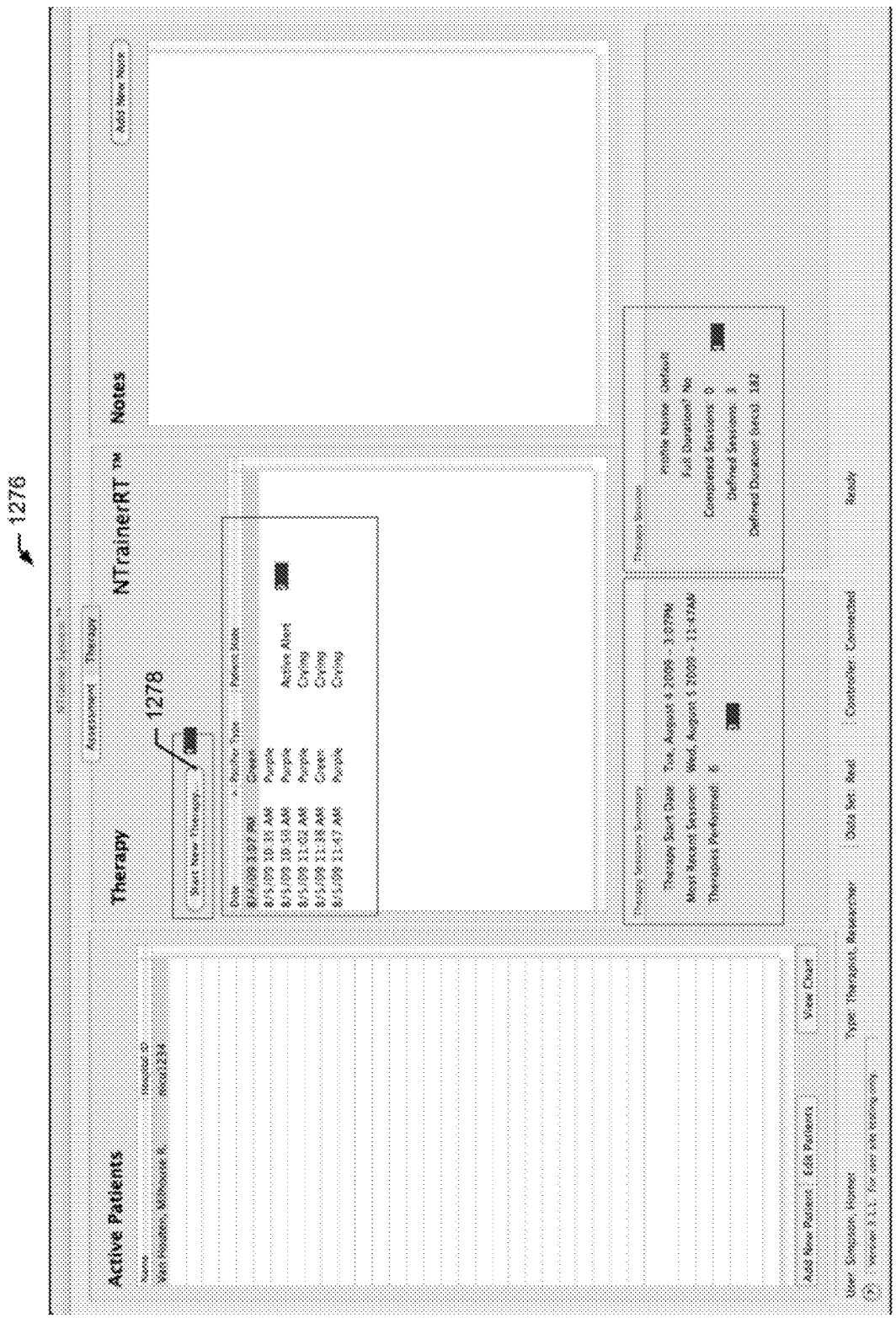
Figure 28:
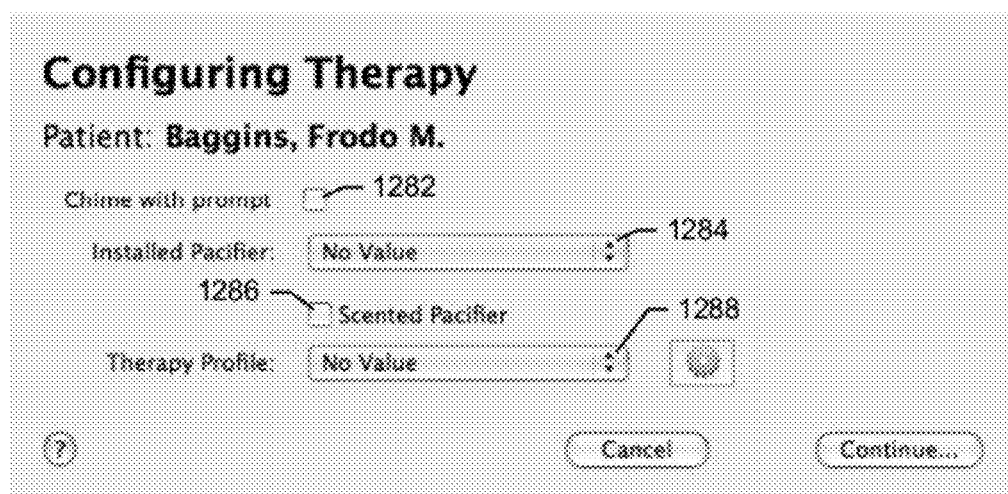

When a therapy session is to be performed, the NNS application system module 300 generates a main therapy GUI input form 1276, as shown in FIG. 27. The main therapy GUI input form 1276 includes a control button 1278 to allow a user to start new therapy session. The main therapy GUI input form 1276 also includes a control button to display previous therapy session data 706 stored in the data source 104, the therapy sessions data 706 includes summaries and detailed information for previous therapy sessions.

In one aspect, the therapy module 304 includes a number of submodules 600-606, including but not limited to a therapy configuration submodule 600, a therapy calibration submodule 602, a therapy execution submodule 604, and a post-therapy review submodule 606. The various submodules 600-606 generate one or more GUI input forms for display that allow the user to configure, execute, and review a therapy session.

The therapy configuration submodule 600, for example, generates a therapy configuration input form 1280. The assessment configuration GUI input form 1280 includes a number controls 1282-1286 related to the therapy session and the pacifier 904 of the orofacial stimulator appliance 108. The assessment configuration GUI input form 1280 also includes a control button 1288 that allows the user to select or modify one or more therapy pulse profiles.

A therapy pulse profile consists of one or more therapeutic waveforms that result in variable but controlled radial displacements of the outer surface of the pacifier 904. The surface displacements of the pacifier 904 provide a tactile stimulus to or near the lips and mouth (e.g., intraoral tissues, anterior tongue blade, anterior tongue dorsum) of the patient to entrain the patient's sCPG to naturally produce an NNS pattern that mimics the generated therapy waveforms.

Preferably, the therapy waveform consists of one or more salient therapeutic bursts and each burst contains two or more square wave pulses. Typically, the bursts are separated by a configurable and variable delay interval.

According to one aspect, the nominal number of pulses in a desired therapeutic burst is six, while the actual number is configurable by users of the NNS system 100. Preferably, each pulse in a therapeutic burst is a square wave pulse having the same configurable amplitude. Further, the period of each pulse increases sequentially thereby, causing the waveform frequency to slow down from the start of the therapeutic burst to the end of the therapeutic burst. A desirable decelerating sequence pulse sequence has periods of approximately 510±3 ms, 526±3 ms, 551±3 ms, 580±3 ms, and 626±3 ms between therapeutic bursts. When more than five pulses are used in the therapeutic burst, the sixth and all subsequent pulses have an periodic interval of approximately 626 ms.

Preferably, each square wave pulse period is shaped to minimize the positive and negative rise/fall times. For example, the transition intervals of each pulse's leading or trailing edges between each pulse may be tuned to create harmonics of 1.7±0.5 Hz, 5.5±0.5 Hz, 9.0±0.5 Hz, 12.5±0.5 Hz, and 16.5±0.5 Hz. It is desired that the therapy waveform have minimal ringing or flutter at the square wave peaks, in order to be perceived as a "clean" square waves. As the therapy pulse profiles may be modified in the amplitude and frequency domains, a power spectrum analysis shows that the preferred therapy waveform generates displacement of the pacifier 904 at a fundamental frequency of approximately 1.7 Hz and higher orders. This fundamental frequency is preferred to entrain the patient's nervous system through cutaneous signal detection. Further, the preferred therapy waveform has a Q factor greater than or equal to ½. As such, the relative high frequency of the rising and falling edges of the therapy pulse helps to achieve stimulus salience in the patient.

In all aspects, the number of square wave pulses per therapeutic burst, the number of therapeutic bursts per therapy session, and the amplitude of the square wave pulses are configurable by the user to account for variability in the patients. For example, the age, endurance, and/or aptitude of the patients may vary, thereby requiring the user to select or modify a therapy pulse profile via the therapy configuration submodule 600.

The therapy calibration submodule 604 functions similar to the assessment calibration submodule 502 and generates a therapy calibration GUI input form similar to the assessment calibration GUI input form 1250. In one aspect, the calibration GUI input form allows the user to communicate with and configure the pulse generation system 106 and the orofacial stimulator appliance 108 to verify the intended function and calibration of the instruments prior to the start of the therapy session.

In one aspect, the expansion characteristics of the therapy pulses as delivered by expansion of the pacifier are verified using a laser micrometer (not shown) in communication with the therapy calibration submodule 604. The data from the laser micrometer regarding the frequency and amplitude components of the therapy pulse at the pacifier 904 may be digitized, recorded, and analyzed by the NNS application 204.

Figure 29:
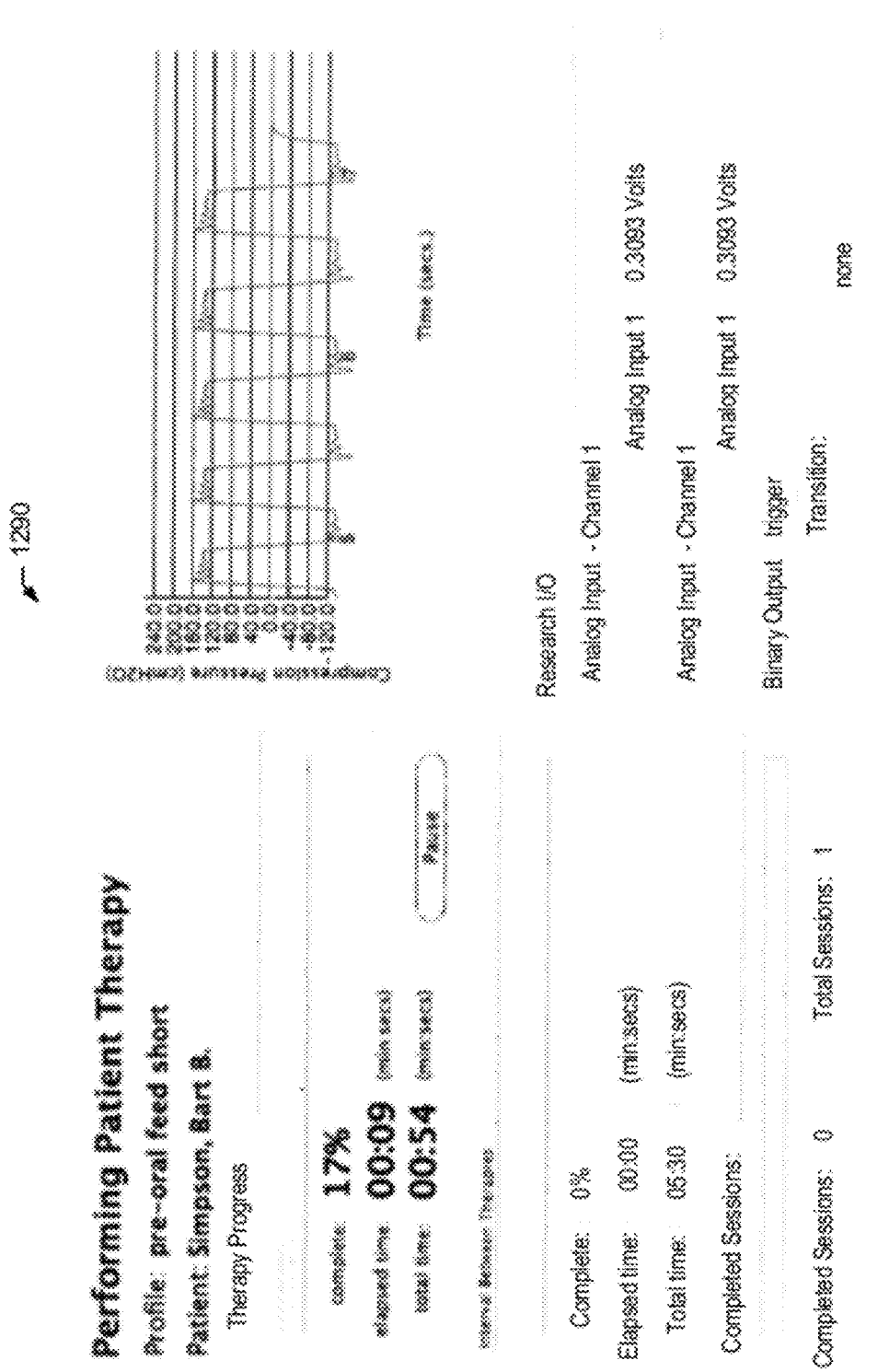

The therapy execution submodule 604 captures and displays the patient's NNS pattern activity during a therapy session. The therapy execution submodule 604 may generate a display 1290, as shown in FIG. 29, that shows progress of the therapy session at the start of the session, during the therapy session, at a rest interval, and at the conclusion of the therapy session, respectively. In other aspects, fewer or a greater number of displays may be provided during the therapy session.

Similar to an assessment session, the therapy session may be initiated by input received through the start control button 1278 of the GUI input form 1276. Alternately, the therapy session may be initiated by a switch on a handpiece 900 of the orofacial stimulator appliance 108.

After a therapy session, the post-therapy review submodule 606 generates a post-session GUI input form similar to the assessment post session GUI input form 1274 where the user inputs notes regarding the therapy session. The user may indicate the state of alertness for the patient, such as alert, crying, drowsy, or sleepy.

The NNS application 204 further includes a leak detection module 306. The leak detection module 306 continuously monitors the performance of pneumatic subsystems within the pulse generator system 104 and the pneumatic lines and connections of the orofacial stimulator appliance 108 to detect air leaks.

Figure 30:
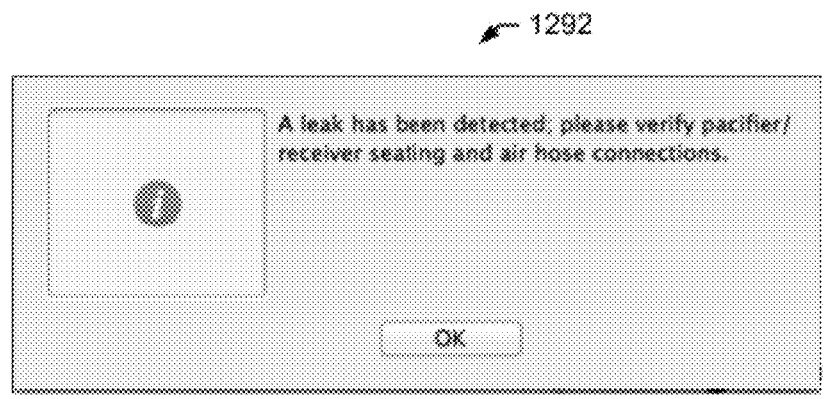

In one aspect, the leak detection module 306 determines that there may be an air leak by identifying reduced pulse amplitudes, increased pulse roll-offs, and/or the need for a greater stroke length in an air pump or pneumatic pulse generator 804 to generate the requested pressure. Further, the leak detection module 306 can identify air leaks caused by disconnected air lines, and poorly seated receiver tubes or pacifiers. The module 306 will display a warning 1292, as shown in FIG. 30, requiring the user to address the leak. The leak detection module 306 may monitor the NNS system 100 automatically and continuously during both assessment and therapy sessions.

The NNS application 204 also includes the research module 308 that allows a user of NNS system 100 to conduct various research experiments and protocols. In particular, the research module 308 receives and transmits data to an input/output (I/O) port of the computing device 102 or the real-time controller 800 of the pulse generation system 106. The I/O port, in turn, may be in communication with any of a variety of external instruments for conducting research.

In various other aspects, the NNS assessment and therapy application 204 may include additional modules for other functions, including those typically associated with medical or rehabilitation facilities. By way of example and not limitation, the NNS application 204 may also include a billing module to interface with an existing billing system or a printing module for printing various data, charts, or reports.

Figure 10:
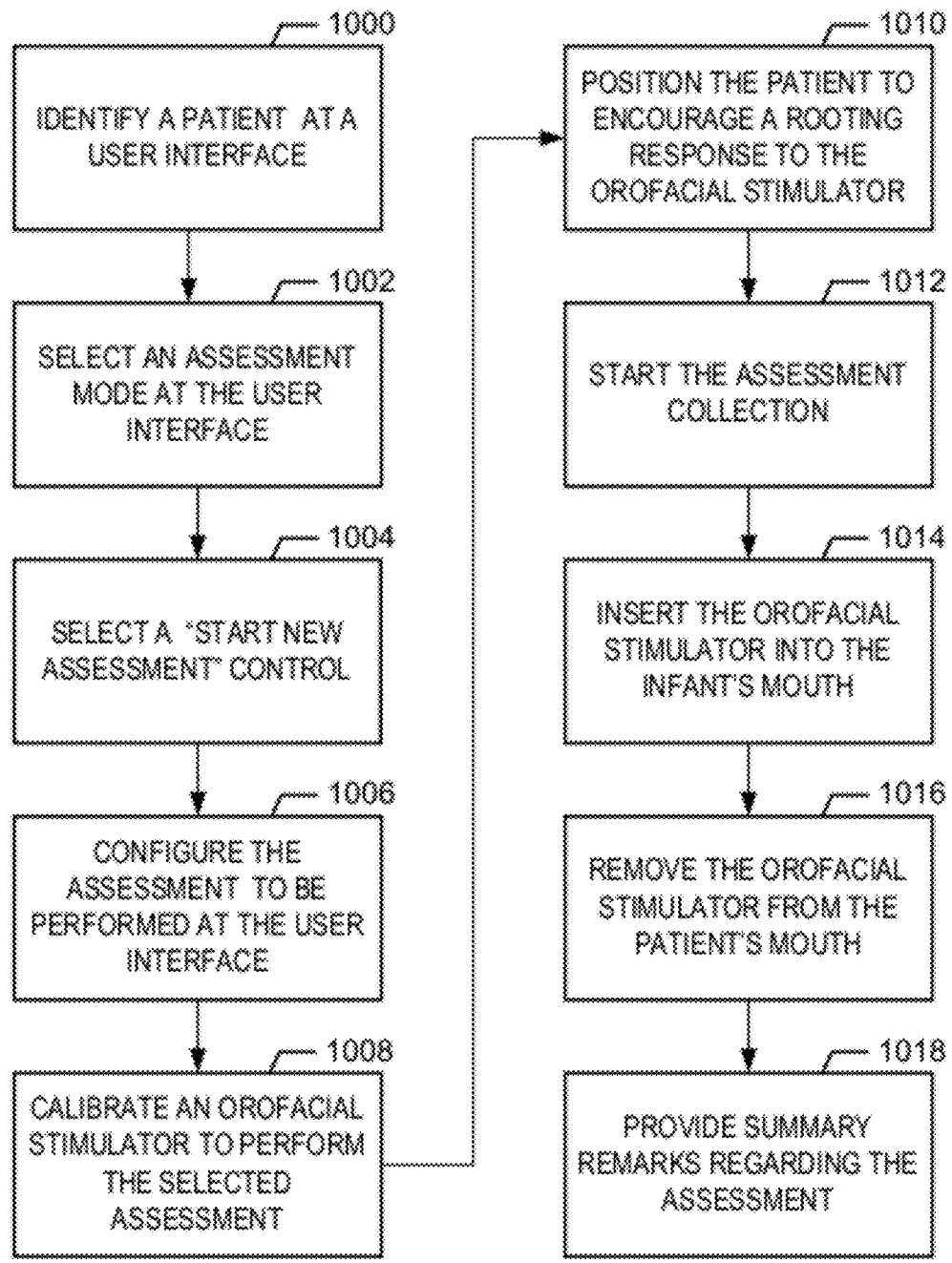
FIG. 10 illustrates a method for assessing a non-nutritive suck pattern according to one aspect of the non-nutritive suck assessment and entrainment system.

FIG. 10 illustrates a method for performing an assessment session to capture and analyze a patient's NNS pattern in accordance with an aspect of the NNS system 100. At step 1000, a user of the NNS system 100 selects a patient from a displayed list of patients. The user then selects a control button to enter the assessment mode of the NNS application 204 at step 1002 and selects the "start new assessment" control button 1224 at step 1004. The assessment session is configured as desired at step 1006 based upon the patient's age, injury, or other patient data 702 and optionally, data 704 regarding the patient's assessment history. The orofacial stimulator appliance 108 is calibrated at step 1008, while the patient is positioned to encourage a rooting response to the orofacial stimulator appliance at step 1010. At step 1012, the assessment session is started, while the orofacial stimulator appliance is contacted with the patient's lips and mouth at step 1014. In other aspects, the orofacial stimulator appliance 108 is inserted into the patient's mouth at step 1014. Similarly, in other aspects, the steps 1012 and 1014 may be reversed.

Once the assessment session is completed, the orofacial stimulator appliance 108 is removed from the patient at step 1016. After the feature extraction submodule 406 analyzes the collected assessment data, using the input form 1274 generated by the post-assessment review module 508. After the assessment session, the user may initiate another assessment session for the same patient or a different patient. Alternatively, the user may instead exit the NNS application 204.

Figure 11:
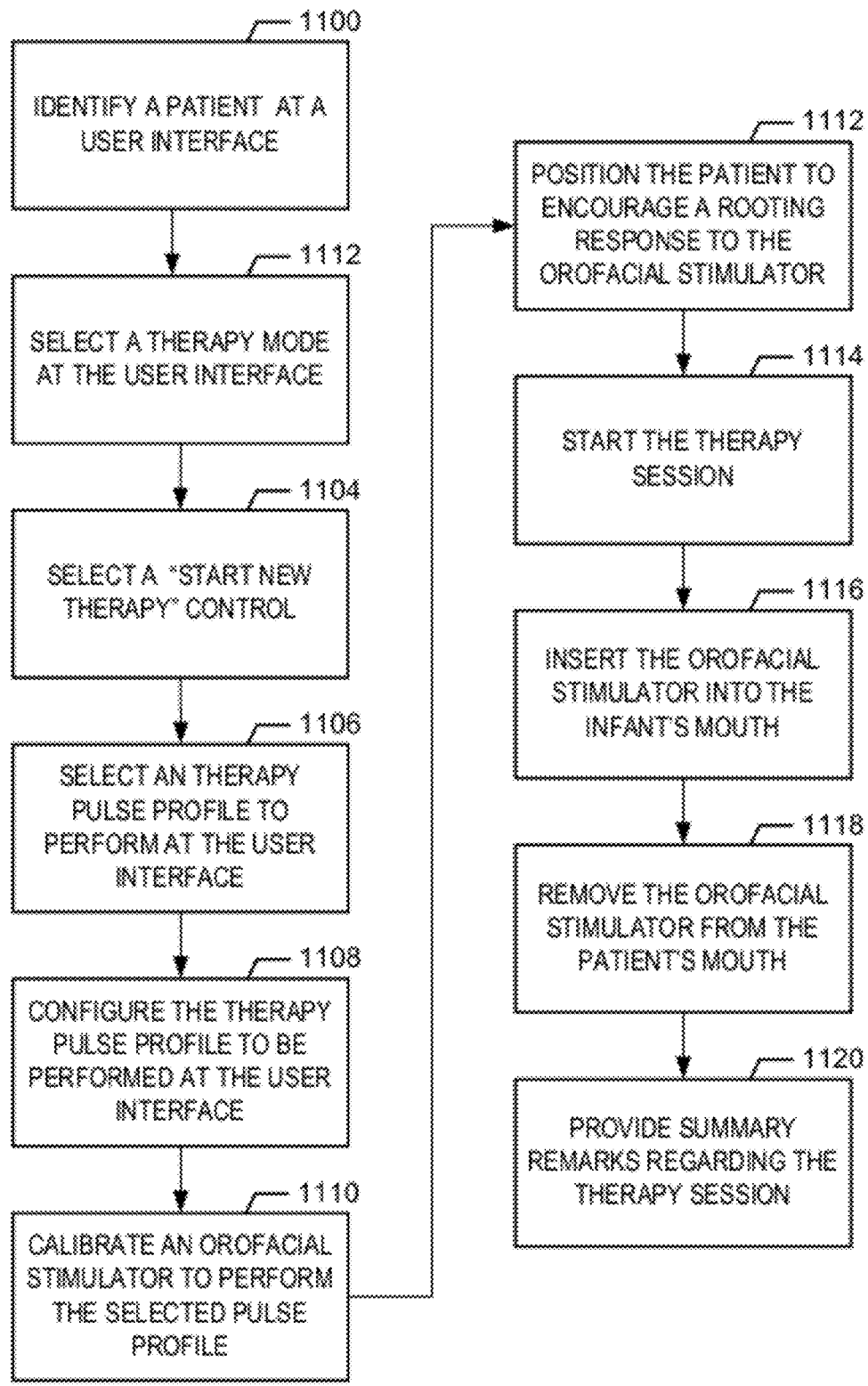
FIG. 11 illustrates a method for stimulating a patient to entrain an organized non-nutritive suck pattern according to one aspect of the non-nutritive suck assessment and entrainment system.

FIG. 11 illustrates a method for performing a therapy session to entrain a patient's sCPG to generate an organized NNS pattern in accordance with an aspect of the NNS system 100. At step 1110, a user of the NNS system 100 selects a patient from a list of patients. The user then selects a control button to enter the therapy mode of the NNS application 204 at step 1102 and the selects a "start new therapy" control button 1278 at step 1104. The therapy pulse profile to be generated during the therapy session is selected from the therapy pulse profile data 708 at step 1106 and at step 1108, the therapy pulse profile is configured as desired based upon the patient's age, injury, or other patient data 702 and any of the patients NNS assessment data 704. The orofacial stimulator appliance 108 is calibrated at step 1110, while the patient is positioned to encourage a rooting response to the orofacial stimulator appliance at step 1112. At step 1114, the therapy session is started, while the orofacial stimulator appliance is contacted with the patient's lips and mouth at step 1116. In other aspects, the orofacial stimulator appliance 108 is inserted into the patient's mouth at step 1116. Similarly, in other aspects, the steps 1114 and 1116 may be reversed. During the therapy session, the user may attempt to hold the patient as still as possible.

Once the therapy session is completed, the orofacial stimulator appliance 108 is removed from the patient at step 1118. The user may provide summary remarks regarding the therapy session at step 1120 using the GUI input form 1274 generated by the post-therapy review module 606. After the therapy session, the user may initiate another therapy session for the same patient or a different patient. Alternatively, the user may instead exit the NNS application 204.

It will be appreciated that the device and method of the present invention are capable of being incorporated in the form of a variety of embodiments, only a few of which have been illustrated and described above. The invention may be embodied in other specific forms without departing from its spirit or essential characteristics. The described embodiments are to be considered in all respects only as illustrative and not restrictive and the scope of the invention is, therefore indicated by the appended claims rather than by the foregoing description. All changes which come within the meaning and range of equivalency of the claims are to be embraced within their scope.

What is claimed is:

1. A non-transitory system executable by a processor for stimulating a CPG and a trigeminal nerve in a human brain, such stimulation influencing brain response or development including repair, control of respiration, control of NNS, mastication, and combinations thereof, in a human brain comprising:
   an assessment module to:
      record a pressure signal received from a pressure transducer in an orofacial stimulator; and,
      generate a display signal to display assessment data based on the received pressure signal;
   a feature extraction module to:
      identify one or more components of a patient's non-nutritive suck pattern in the pressure signal;
      determine a symmetry of the patient's non-nutritive suck pattern;
      determine a repetition of the patient's non-nutritive suck pattern; and,
      assign a spatiotemporal index value to the patient's non-nutritive suck pattern, the spatiotemporal index value indicating an overall rating of the patient's non-nutritive suck pattern; and,
   a therapy module to:
      generate a therapeutic pressure pulse signal comprising a base frequency signal further comprising two or more pressure pulses, wherein each pressure pulse causes a displacement of a pacifier surface contacted by the lip and the mouth of the patient, wherein each of the two or more pressure pulses has a square wave profile and are separated by an interval between 500 milliseconds and 650 milliseconds in duration;
      generate a therapeutic pressure profile signal comprising at least one of the therapeutic pressure pulse signals; and,
      transmit the therapeutic pressure pulse profile signal to the orofacial stimulator.

2. The system of claim 1, wherein the base frequency is between 1.5 Hz and 5 Hz.

3. The system of claim 2, wherein the two or more pressure pulses causes surface motion of between about 260 microns and 300 microns, with changes in the motion occurring at an interval between 20 milliseconds and 50 milliseconds.

4. The system of claim 3, wherein the therapeutic pressure profile comprises at least 6 pressure pulses in succession contacted with the patient for at least two minutes, at least twice a day.

5. The system of claim 2, wherein each of the two or more pressure pulses comprises a higher order harmonic of the base frequency.

6. The system of claim 5, wherein the higher order harmonic decay for the two or more pressure pulses vary in an amplitude and a frequency.

7. The system of claim 5, wherein the higher order harmonic decay for the two or more pressure pulses are identical in an amplitude and a frequency.

8. The system of claim 2, wherein each of the two or more pressure pulses has a first order under damped response square wave profile.

9. The system of claim 8, wherein the under damped square wave profile of the two or more pressure pulses has a Q factor greater than or equal to ½.

10. The system of claim 1, wherein the pressure transducer generates the pressure signal in response to pressure applied to the orofacial stimulator.

11. The system of claim 1, wherein the display signal contains waveform data, wherein the waveform data indicates at least one event in the pressure signal.

12. The system of claim 11, wherein the at least one event is identified as a pressure peak, a non-nutritive suck event, a burst, a chew, or combinations thereof.

13. The system of claim 1, wherein the spatiotemporal index value is based upon one or more suck symmetries, a suck quantity, and a burst timing of the patient's non-nutritive suck pattern.

14. The system of claim 1, wherein the system further comprises a calibration module to calibrate the orofacial stimulator.

15. The system of claim 14, wherein the orofacial stimulator appliance is calibrated prior to: receiving pressure signals at the assessment module, generating the therapeutic pressure pulse signal, or both.

16. The system of claim 14, wherein the orofacial stimulator appliance is calibrated after: receiving pressure signals at the assessment module, generating the therapeutic pressure pulse signal, or both.

17. The system of claim 14, wherein the orofacial stimulator appliance is calibrated prior to and after: receiving pressure signals at the assessment module, generating the therapeutic pressure pulse signal, or both.

18. The system of claim 1, wherein the system further comprises a review module to review at least one of the assessment data, the generated therapeutic pressure profile, or both.

19. The system of claim 1, wherein the transmitted therapeutic pressure pulse profile signal is received at at least one of the pneumatic pressure transducer and the orofacial stimulator appliance.

20. A processing system encoded with an application for stimulating a CPG and a trigeminal nerve in a human brain, such stimulation influencing brain response or development including repair, control of respiration, control of NNS, mastication, and combinations thereof, in a human brain, the system comprising:
a processor;
memory; and,
the application, executable by the processor, further comprising instructions to:
record a pressure signal received from a pressure transducer in an orofacial stimulator;
generate a display signal to display assessment data based on the received pressure signal;
identify one or more components of a patient's non-nutritive suck pattern in the pressure signal;
determine a symmetry of the patient's non-nutritive suck pattern;
determine a repetition of the patient's non-nutritive suck pattern;
assign a spatiotemporal index value to the patient's non-nutritive suck pattern, the spatiotemporal index value indicating an overall rating of the patient's non-nutritive suck pattern;
generate a therapeutic pressure pulse signal comprising a base frequency signal further comprising two or more pressure pulses, wherein a first pressure pulse causes a positive displacement of a pacifier surface contacted by a lip and a mouth of the patient and a second pressure pulse causes a negative displacement of the pacifier surface contacted by the lip and the mouth of the patient, wherein each of the two or more pressure pulses has a damped square wave profile and are separated by an interval between 500 milliseconds and 650 milliseconds in duration;
generate a therapeutic pressure profile signal comprising at least one of the therapeutic pressure pulse signals; and,
transmit the therapeutic pressure pulse profile signal to the orofacial stimulator.

21. The system of claim 20, wherein the base frequency is between 1.5 Hz and 5 Hz.

22. The system of claim 21, wherein the two or more pressure pulses causes surface motion of between about 260 microns and 300 microns, with changes in the motion occurring at an interval between 20 milliseconds and 50 milliseconds.

23. The system of claim 22, wherein the therapeutic pressure profile comprises at least 6 pressure pulses in succession contacted with the patient for at least two minutes, at least twice a day.

24. The system of claim 21, wherein each of the two or more pressure pulse is a higher order harmonic decay of the base frequency.

25. The system of claim 24, wherein the higher order harmonic for the two or more pressure pulses varies in an amplitude and a frequency.

26. The system of claim 24, wherein the higher order harmonic for the two or more pressure pulses is identical in an amplitude and a frequency.

27. The system of claim 21, wherein each of the two or more pressure pulses has an under damped square wave profile.

28. The system of claim 27, wherein the under damped square wave profile of the two or more pressure pulses has a Q factor greater than or equal to ½.

29. The system of claim 20, wherein the pressure transducer generates the pressure signal in response to pressure applied to the orofacial stimulator.

30. The system of claim 20, wherein the display signal contains waveform data, wherein the waveform data indicates at least one event in the pressure signal.

31. The system of claim 30, wherein the at least one event is identified as a pressure peak, a non-nutritive suck event, a burst, a chew, or combinations thereof.

32. The system of claim 20, wherein the spatiotemporal index value is based upon a suck symmetry, a suck quantity, and a burst timing of the patient's non-nutritive suck pattern.

33. The system of claim 20, wherein the system further comprises a calibration module to calibrate the orofacial stimulator.

34. The system of claim 33, wherein the orofacial stimulator appliance is calibrated prior to: receiving pressure signals at the assessment module, generating the therapeutic pressure pulse signal, or both.

35. The system of claim 33, wherein the orofacial stimulator appliance is calibrated after: receiving pressure signals at the assessment module, generating the therapeutic pressure pulse signal, or both.

36. The system of claim 33, wherein the orofacial stimulator appliance is calibrated prior to and after: receiving pressure signals at the assessment module, generating the therapeutic pressure pulse signal, or both.

37. The system of claim 20, wherein the system further comprises a review module to review at least one of the assessment data, the generated therapeutic pressure profile, or both.

38. The system of claim 20, wherein the transmitted therapeutic pressure pulse profile signal is received at a pressure transducer.

39. A non-transitory computer readable medium encoded with instructions for operating a system for delivering a non-nutritive suck stimulus to a patient, the instructions executable by a processor in communication with memory and comprising:
   receiving, at the processor, a pressure signal received from a pressure transducer in an orofacial stimulator appliance;
   generating a display signal to display assessment data based on the received pressure signal;
   identifying one or more components of the patient's non-nutritive suck pattern in the pressure signal;
   determining a symmetry of the patient's non-nutritive suck pattern;
   determining a repetition of the patient's non-nutritive suck pattern;
   assigning a spatiotemporal index value to the patient's non-nutritive suck pattern, the spatiotemporal index value indicating an overall rating of the patient's non-nutritive suck pattern;
   generating a therapeutic pressure pulse signal;
   generating a therapeutic pressure profile signal comprising at least one of the therapeutic pressure pulse signals; and,
   transmitting the therapeutic pressure pulse profile signal to the orofacial stimulator appliance.

40. A non-transitory system executable by a processor for stimulating a human brain to organize a patient's non-nutritive suck pattern, the system comprising:
   an assessment module to:
      record a pressure signal received from a pressure transducer in an orofacial stimulator appliance;
   a feature extraction module to:
      identify one or more components of the patient's non-nutritive suck pattern in the pressure signal; and
      assign a spatiotemporal index value to the patient's non-nutritive suck pattern; and,
   a therapy module to:
      generate a therapeutic pressure pulse signal comprising a damped square wave profile;
      transmit the therapeutic pressure pulse profile signal to the orofacial stimulator appliance.

41. A processing system encoded with an application for stimulating a human brain to organize a patient's non-nutritive suck pattern, the system comprising:
   a processor;
   memory; and,
   the application, executable by the processor, further comprising instructions to:
      record a pressure signal received from a pressure transducer in an orofacial stimulator appliance;
      identify one or more components of a patient's non-nutritive suck pattern in the pressure signal;
      assign a spatiotemporal index value to the patient's non-nutritive suck pattern, the spatiotemporal index value indicating an overall rating of the patient's non-nutritive suck pattern;
      generate a therapeutic pressure pulse signal comprising a damped square wave; and,
      transmit the therapeutic pressure pulse profile signal to the orofacial stimulator appliance.

42. A non-transitory computer readable medium encoded with instructions for operating a system for delivering a non-nutritive suck stimulus to a patient, the instructions executable by a processor in communication with memory and comprising:
   receiving, at the processor, a pressure signal received from a pressure transducer in an orofacial stimulator appliance;
   identifying one or more components of the patient's non-nutritive suck pattern in the pressure signal;
   determining a symmetry of the patient's non-nutritive suck pattern;
   determining a repetition of the patient's non-nutritive suck pattern;
   assigning a spatiotemporal index value to the patient's non-nutritive suck pattern, the spatiotemporal index value indicating an overall rating of the patient's non-nutritive suck pattern;
   generating a therapeutic pressure pulse signal; and,
   transmitting the therapeutic pressure pulse profile signal to the orofacial stimulator appliance.

43. The system of claim 42, wherein the instructions further comprise:
   verify an expansion characteristic of the orofacial stimulator appliance in response to the therapeutic pressure pulse profile signal, wherein verification is performed by measuring a frequency and an amplitude component of a motion of the orofacial stimulator appliance.

44. The system of claim 43, wherein the instructions further comprise digitizing and recording the frequency and amplitude components.

45. The system of claim 43, wherein the frequency and the amplitude are measured by a laser micrometer.

46. A processing system encoded with an application for stimulating a human brain to organize a patient's non-nutritive suck pattern, the system comprising:
   a processor;
   memory; and,
   the application, executable by the processor, further comprising instructions to:
      record a pressure signal received from a pressure transducer in an orofacial stimulator appliance;
      identify one or more components of a patient's non-nutritive suck pattern in the pressure signal;
      generate a therapeutic pressure pulse signal; and,
      transmit the therapeutic pressure pulse profile signal to the orofacial stimulator appliance.

* * * * *